US012331006B2

(12) United States Patent
Silverman et al.

(10) Patent No.: US 12,331,006 B2
(45) Date of Patent: Jun. 17, 2025

(54) PROCESS FOR THE SYNTHESIS OF (S) 3-AMINO-4-(DIFLUOROMETHYLENYL)-CYCLOPENT-1-ENE-1-CARBOXYLIC ACID

(71) Applicant: NORTHWESTERN UNIVERSITY, Evanston, IL (US)

(72) Inventors: Richard B. Silverman, Winnetka, IL (US); Matthew Moschitto, Gloucester, MA (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 897 days.

(21) Appl. No.: 16/950,542

(22) Filed: Nov. 17, 2020

(65) Prior Publication Data

US 2021/0139412 A1    May 13, 2021

Related U.S. Application Data

(62) Division of application No. 16/423,761, filed on May 28, 2019, now Pat. No. 10,836,708.

(60) Provisional application No. 62/676,373, filed on May 25, 2018, provisional application No. 62/814,026, filed on Mar. 5, 2019, provisional application No. 62/835,776, filed on Apr. 18, 2019.

(51) Int. Cl.
| | | |
|---|---|---|
| *C07C 227/16* | (2006.01) | |
| *C07C 227/20* | (2006.01) | |
| *C07C 229/48* | (2006.01) | |
| *C07C 269/06* | (2006.01) | |
| *C07C 271/24* | (2006.01) |

(52) U.S. Cl.
CPC .......... *C07C 227/16* (2013.01); *C07C 229/48* (2013.01)

(58) Field of Classification Search
CPC ................ C07C 227/16; C07C 229/48; C07C 2601/10; C07C 227/20; C07C 269/06; C07C 271/24
See application file for complete search history.

(56) References Cited

U.S. PATENT DOCUMENTS

| | | | |
|---|---|---|---|
| 6,794,413 B1 | 9/2004 | Silverman et al. | |
| 7,381,748 B1 | 6/2008 | Silverman et al. | |
| 8,969,413 B2 | 3/2015 | Silverman et al. | |
| 9,670,141 B2 * | 6/2017 | Silverman | A61P 25/36 |
| 9,993,449 B2 * | 6/2018 | Silverman | C07C 229/48 |
| 10,836,708 B2 | 11/2020 | Silverman et al. | |
| 2017/0101364 A1 * | 4/2017 | Silverman | A61P 25/28 |

FOREIGN PATENT DOCUMENTS

| WO | 2008023364 A1 | 2/2008 |
|---|---|---|
| WO | 2016073983 A2 | 5/2016 |

OTHER PUBLICATIONS

Juncosa et al., "Design and Mechanism of (S)-3-Amino-4-(difluoromethylenyl)cyclopent-1-ene-1-carboxylic Acid, a highly Potent γ-Aminobutyric Acid Aminotransferase Inacitivator for the Treatment of Addiction", J. Am. Chem. Soc. (2018), 140: pp. 2151-2164. (Year: 2018).*
Cheraiet, Z., S. Quarna, S. Hessainia, M. Berredjem and N. Aouf, "N-tert-Butoxycarbonylation of Structurally Diverse Amines and Sulfamides under Water-Mediated Catalyst-Free Conditions", ISRN Organic Chemistry 2012; Article ID 404235, pp. 1-8. (Year: 2012).*
International Search Report and Written Opinion of the International Searching Authority, dated Sep. 10, 2019, corresponding to counterpart International Application No. PCT/US2019/034140; 8 total pages.
Lippert, et al., "4-Amino-hex-5-enoic Acid, a Selective Catalytic Inhibitor of 4-Aminobutyric-Acid Aminotransferase in Mammalian Brain", Eur. J. Biochem, vol. 74, No. 3; Apr. 15, 1977; pp. 441-445.
Notification concerning Transmittal of International Preliminary Report on Patentability (Chapter I of the Patent Cooperation Treaty), dated Apr. 19, 2018, including International Preliminary Report on Patentability, and Written Opinion and International Search Report of the International Searching Authority, corresponding to International Application No. PCT/US2016/056245; 13 total pages.
International Search Report and Written Opinion of the International Searching Authority, corresponding to International Application No. PCT/US2016/056245, dated Jan. 26, 2017; 16 total pages.
Qiu et al., "A New Class of Conformationally Rigid Analogues of 4-Amino-5-halopentanoic Acids, Potent Inactivators of γ-Aminobutyric Acid Aminotransferase," J. Med. Chem. (2000), vol. 43; pp. 706-720.
Pan et al., "Design, Synthesis, and Biological Activity of a Difluoro-Substituted, Conformationally Rigid Vigabatrin Analogue as a Potent γ-Aminobutyric Acid Aminotransferase Inhibitor", Journal of Medicinal Chemistry, vol. 46, No. 25, Dec. 4, 2003;pp. 5292-5293.
Juncosa et al., "Design and and Mechanism of (S)-3-Amino-4-(difluoromethylenyl)cyclopent-1-ene-1-carboxylic Acid, a Highly Potent γ-Aminobutyric Acid Aminotransferase Inactivator for the Treatment of Addiction," Journal of the American ChemicalSociety (2018), vol. 140; pp. 2151-2164.
Lu, et al., "Fluorinated Conformationally-Restricted γ-Aminobutyric Acid Aminotransferase Inhibitors", Journal of Medicinal Chemistry, E-Pub, vol. 49, No. 25, Oct. 11, 2006; pp. 7404-7412 and Figures 1-2.
Zhao et al., "Difluoromethyl 2-Pyridyl Sulfone: A New gem-Difluoroolefination Reagent for Aldehydes and Ketones,"—Organic Letters (2010), vol. 12, No. 7; pp. 1444-1447.
Zhou et al., "Direct Synthesis of Fluorinated Heteroarylether Bioisosteres,", Angew. Chem. Int. Ed. (2013), vol. 52; pp. 3949-3952.
Yuan, Hai, et al., "Structural modifications of (1S, 3S)-3-amino-4-difluoromethylenecyclopentanecarboxylic acid, a potent irreversible inhibitor of GABA aminotransferase," Bioorganic & medicinal chemistry letters, Mar. 2007, pp. 1651-1654, 17,6.

(Continued)

*Primary Examiner* — Samantha L. Shterengarts
*Assistant Examiner* — Sagar Patel
(74) *Attorney, Agent, or Firm* — Carter, DeLuca & Farrell LLP

(57) ABSTRACT

Provided herein are processes, compounds and compositions for making (S)-3-amino-4-(difluoromethylenyl)cyclopent-1-ene-1-carboxylic acid. Also provided herein a pharmaceutical compositions containing (S)-3-amino-4-(difluoromethylenyl)cyclopent-1-ene-1-carboxylic acid.

12 Claims, 6 Drawing Sheets

(56) References Cited

OTHER PUBLICATIONS

Office Action from related Indian case 202017051019, Jun. 10, 2022, 6 pages.
English translation of Korean Office Action for application No. 10-2020-7037246, Jun. 11, 2024, 15 pages.
Extended European Search Report for application No. 24175100.7, Nov. 29, 2024, 6 pages.

\* cited by examiner

¹⁹F (CDCl₃; 127.5 MHz) (9)

¹H (CDCl₃, 500 MHz) (1)

$^{13}$C (CDCl$_3$; 126 MHz) 1

$^{19}$F (CDCl$_3$; 127.5 MHz) 1

PROCESS FOR THE SYNTHESIS OF (S) 3-AMINO-4-(DIFLUOROMETHYLENYL)-CYCLOPENT-1-ENE-1-CARBOXYLIC ACID

CROSS-REFERENCE TO RELATED APPLICATIONS

This application is a divisional application of U.S. patent application Ser. No. 16/423,761, filed May 28, 2019, now U.S. Pat. No. 10,836,708, which claims benefit of and priority to U.S. Provisional Application No. 62/676,373, filed May 25, 2018; and U.S. Provisional Application No. 62/814,026, filed Mar. 5, 2019; which are each incorporated herein by reference in their entireties; and to U.S. Provisional Application No. 62/835,775, filed Apr. 18, 2019.

This invention was made with government support under R01 DA030604 awarded by the National Institutes of Health. The government has certain rights in the invention.

TECHNICAL FIELD

Synthesis of (S)-3-amino-4-(difluoromethylenyl)cyclopent-1-ene-1-carboxylic acid.

BACKGROUND (S)-3-Amino-4-(difluoromethylenyl)cyclopent-1-ene-1-carboxylic acid is an inhibitor of γ-aminobutyric acid aminotransferase (GABA-AT) and has been shown as a possible treatment of epilepsy, addiction and hepatocellular carcinoma. See, e.g., U.S. Pat. No. 9,670,141 and Juncosa et al., J. Am. Chem. Soc. 2018, 140, 2151-2164. GABA is an inhibitory neurotransmitter in the central nervous system (CNS). When GABA concentrations in the brain drop below a threshold level, convulsions can occur. Increasing GABA levels has been shown to stop convulsions. Additionally, increased concentrations of GABA antagonize the release of dopamine from the nucleus accumbens, a region of the hypothalamus associated with reward and motivation, and have been suggested as a possible treatment of addiction. Unfortunately, direct administration of GABA is not viable as GABA does not cross the blood brain barrier. GABA concentrations, however, can be increased by inhibiting GABA aminotransferase (GABA-AT). 4-Aminohex-5-enoic acid, also known as vigabatrin (marketed as Sabril®), currently is the only FDA approved inhibitor of GABA-AT for the treatment of infantile spasms and has been shown as a possible treatment of addiction. Vigabatrin, however, requires a large dose (1-3 g/day), inhibits multiple GABA receptors, and, with prolonged use, causes retinal damage in 25-40% of patients.

In vivo studies in rats indicate that (S)-3-amino-4-(difluoromethylenyl)cyclopent-1-ene-1-carboxylic acid is superior to previous inhibitors of GABA-AT at suppressing the release of dopamine in the corpus striatum after exposure to cocaine or nicotine. (S)-3-Amino-4-(difluoromethylenyl)cyclopent-1-ene-1-carboxylic acid does not inhibit off-target aminotransferase enzymes like alanine aminotransferase and aspartate aminotransferase. It additionally does not inhibit the hERG potassium ion channel or various microsomal cytochrome P450 enzymes.

According existing techniques, (S)-3-amino-4-(difluoromethylenyl)cyclopent-1-ene-1-carboxylic acid has been synthesized in six steps from (1S,3S)-3-amino-4-(difluoromethylidene)cyclopentane-1-carboxylic acid (also known as CPP-115).

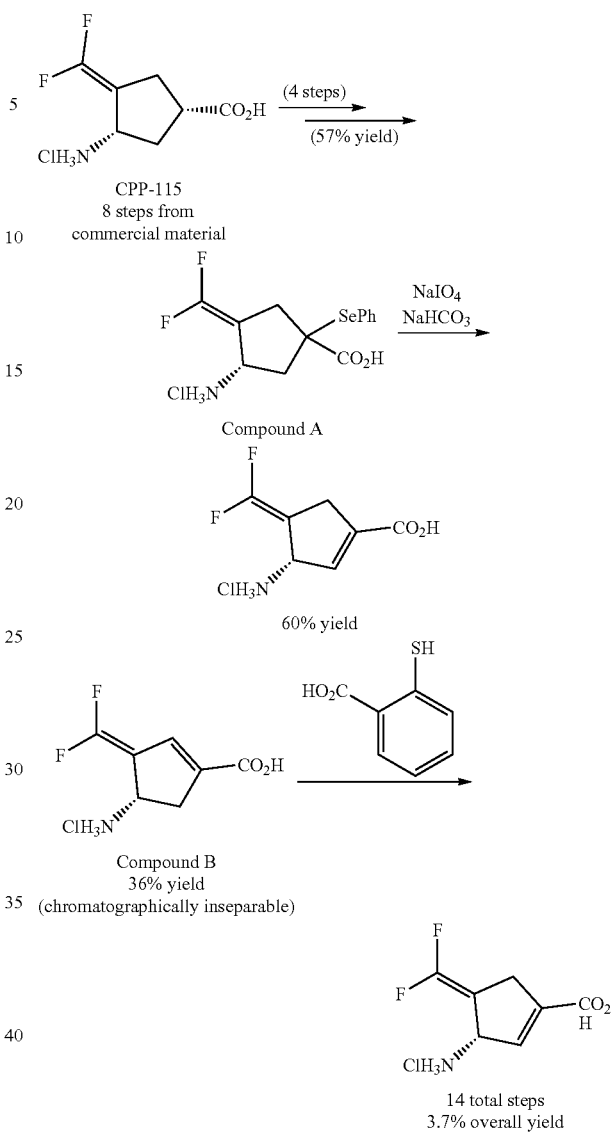

See also, e.g., Juncosa et al., J. Am. Chem. Soc., supra, and U.S. Pat. Nos. 7,381,748, 6,794,413 and 9,670,141, each incorporated herein by reference in their entireties.

CPP-115 is an inhibitor of GABA-AT and currently in clinical trials for the treatment of epilepsy. It has been determined that (S)-3-amino-4-(difluoromethylenyl)cyclopent-1-ene-1-carboxylic acid is 9.8 times more efficient as an activator of GABA-AT than CPP-115. Since synthesis of CPP-115 takes 8-steps, the total synthetic step count from commercial starting material to (S)-3-amino-4-(difluoromethylenyl)cyclopent-1-ene-1-carboxylic acid is fourteen with an overall yield of 3.7%. The synthesis of CPP-115 involves the use of the highly flammable tert-butyl lithium (on gram scale) to install the 1,1'-difluoroolefin, which limits the scale at which the reaction can be run. Furthermore, the existing synthesis relies of the introduction of the cyclopentene through selenoxide elimination. Protected CPP-115 is selenated in 70% yield, although yields can vary depending on scale. α-Elimination of Compound A yields a mixture of chromatographically inseparable isomers in a 5:3 ratio favoring (S)-3-amino-4-(difluoromethylenyl)cyclopent-1-ene-1-carboxylic acid. Compound B is selectively degraded using thiosalicylic acid to produce solely (S)-3-amino-4-(difluoromethylenyl)cyclopent-1-ene-1-carboxylic acid in an overall yield of 36% from Compound A. Only small batches of (S)-3-amino-4-(difluoromethylenyl)cyclopent-1-ene-1-carboxylic acid can be obtained using the existing technique. Additionally, since selenium is toxic and regulated by the FDA to levels below 80-150 µg/day, the production of selenol in the penultimate step complicates the synthesis and purification of (S)-3-amino-4-(difluoromethylenyl)cyclopent-1-ene-1-carboxylic acid.

Accordingly, there is a need for processes that are better suited for larger scale preparation of (S)-3-amino-4-(difluoromethylenyl)cyclopent-1-ene-1-carboxylic acid that will reduce costs, decrease the number of manufacturing steps, decrease hazardous environmental waste, and increase efficiency of manufacture.

SUMMARY

A process for preparing (S)-3-amino-4-(difluoromethylenyl)cyclopent-1-ene-1-carboxylic acid (1) or salt thereof is provided which includes converting ((1R,4S)-2-azabicyclo[2.2.1]hept-5-en-3-one) (2) to (1R,4S)-2-(4-methoxybenzyl)-2-azabicyclo[2.2.1]hept-5-en-3-one (3). (1R,4S)-2-(4-Methoxybenzyl)-2-azabicyclo[2.2.1]hept-5-en-3-one (3) is converted to (1R,4R,6S,7R)-7-bromo-2-(4-methoxybenzyl)-3-oxo-2-azabicyclo[2.2.1]heptan-6-yl acetate (4). (1R,4R,6S,7R)-7-Bromo-2-(4-methoxybenzyl)-3-oxo-2-azabicyclo[2.2.1]heptan-6-yl acetate (4) is converted to (1R,4R,7R)-7-bromo-2-(4-methoxybenzyl)-2-azabicyclo[2.2.1]heptane-3,6-dione (5). (1R,4R,7R)-7-Bromo-2-(4-methoxybenzyl)-2-azabicyclo[2.2.1]heptane-3,6-dione (5) is converted to (1R,4R,7R)-7-bromo-6-(difluoromethylene)-2-(4-methoxybenzyl)-2-azabicyclo[2.2.1]heptan-3-one (6). (1R,4R,7R)-7-Bromo-6-(difluoromethylene)-2-azabicyclo[2.2:1]heptan-3-one (6) is converted to (1R,4R,7R)-7-bromo-6-(difluoromethylene)-2-azabicyclo[2.2.1]heptan-3-one (7). (1R,4R,7R)-7-Bromo-6-(difluoromethylene)-2-azabicyclo[2.2.1]heptan-3-one (7) is converted to (1R,4R,7R)-7-bromo-6-(difluoromethylene)-2-(tert-butoxycarbonyl)-2-azabicyclo[2.2.1]heptan-3-one (8). (1R,4R,7R)-7-Bromo-6-(difluoromethylene)-2-(tert-butoxycarbonyl)-2-azabicyclo[2.2.1]heptan-3-one (8) is converted to methyl (S)-3-((tert-butoxycarbonyl)amino)-4-(difluoromethylene)cyclopent-1-ene-1-carboxylate (9). Methyl (S)-3-((tert-butoxycarbonyl)amino)-4-(difluoromethylene)cyclopent-1-ene-1-carboxylate (9) is converted to (S)-3-amino-4-(difluoromethylenyl)cyclopent-1-ene-1-carboxylic acid (1).

(S)-3-Amino-4-(difluoromethylenyl)cyclopent-1-ene-1-carboxylic acid (1) is made by a process described herein. Compositions including (S)-3-amino-4-(difluoromethylenyl)cyclopent-1-ene-1-carboxylic acid (1) are described herein. Pharmaceutical compositions including (S)-3-amino-4-(difluoromethylenyl)cyclopent-1-ene-1-carboxylic acid (1) are described herein.

(1R,4S)-2-(4-Methoxybenzyl)-2-azabicyclo[2.2.1]hept-5-en-3-one (3) is provided herein. Compositions including (1R,4S)-2-(4-methoxybenzyl)-2-azabicyclo[2.2.1]hept-5-en-3-one (3) are provided herein. Pharmaceutical compositions including (1R,4S)-2-(4-methoxybenzyl)-2-azabicyclo[2.2.1]hept-5-en-3-one (3) are provided herein. (1R,4S)-2-(4-Methoxybenzyl)-2-azabicyclo[2.2.1]hept-5-en-3-one (3) is made by a process disclosed herein.

(1R,4R,6S,7R)-7-Bromo-2-(4-methoxybenzyl)-3-oxo-2-azabicyclo[2.2.1]heptan-6-yl acetate (4) is provided herein. Compositions including (1R,4R,6S,7R)-7-bromo-2-(4-methoxybenzyl)-3-oxo-2-azabicyclo[2.2.1]heptan-6-yl acetate (4) are provided herein. Pharmaceutical compositions including (1R,4R,6S,7R)-7-bromo-2-(4-methoxybenzyl)-3-oxo-2-azabicyclo[2.2.1]heptan-6-yl acetate (4) are provided herein. (1R,4R,6S,7R)-7-Bromo-2-(4-methoxybenzyl)-3-oxo-2-azabicyclo[2.2.1]heptan-6-yl acetate (4) is made by a process disclosed herein.

(1R,4R,7R)-7-Bromo-2-(4-methoxybenzyl)-2-azabicyclo[2.2.1]heptane-3,6-dione (5) is provided herein. Compositions including (1R,4R,7R)-7-bromo-2-(4-methoxybenzyl)-2-azabicyclo[2.2.1]heptane-3,6-dione (5) are provided herein. Pharmaceutical compositions including (1R,4R,7R)-7-bromo-2-(4-methoxybenzyl)-2-azabicyclo[2.2.1]heptane-3,6-dione (5) are provided herein. (1R,4R,7R)-7-Bromo-2-(4-methoxybenzyl)-2-azabicyclo[2.2.1]heptane-3,6-dione (5) is made by a process described herein.

(1R,4R,7R)-7-Bromo-6-(difluoromethylene)-2-(4-methoxybenzyl)-2-azabicyclo[2.2.1]heptan-3-one (6) is provided herein. Compositions including (1R,4R,7R)-7-bromo-6-(difluoromethylene)-2-azabicyclo[2.2.1]heptan-3-one (6) are provided herein. Pharmaceutical compositions including (1R,4R,7R)-7-bromo-6-(difluoromethylene)-2-azabicyclo[2.2.1]heptan-3-one (6) are provided herein. (1R,4R,7R)-7-Bromo-6-(difluoromethylene)-2-(4-methoxybenzyl)-2-azabicyclo[2.2.1]heptan-3-one (6) is made by a process described herein.

(1R,4R,7R)-7-Bromo-6-(difluoromethylene)-2-azabicyclo[2.2.1]heptan-3-one (7) is provided herein. Compositions including (1R,4R,7R)-7-bromo-6-(difluoromethylene)-2-azabicyclo[2.2.1]heptan-3-one (7) are provided herein. Pharmaceutical compositions including (1R,4R,7R)-7-bromo-6-(difluoromethylene)-2-azabicyclo[2.2.1]heptan-3-one (7) are provided herein. (1R,4R,7R)-7-Bromo-6-(difluoromethylene)-2-azabicyclo[2.2.1]heptan-3-one (7) is made by a process described herein.

(1R,4R,7R)-7-Bromo-6-(difluoromethylene)-2-(tert-butoxycarbonyl)-2-azabicyclo[2.2.1]heptan-3-one (8) is provided herein. Compositions including (1R,4R,7R)-7-bromo-6-(difluoromethylene)-2-(tert-butoxycarbonyl)-2-azabicyclo[2.2.1]heptan-3-one (8) are provided herein. Pharmaceutical compositions including (1R,4R,7R)-7-bromo-6-(difluoromethylene)-2-(tert-butoxycarbonyl)-2-azabicyclo[2.2.1]heptan-3-one (8) are provided herein. 1R,4R,7R)-7-Bromo-6-(difluoromethylene)-2-(tert-butoxycarbonyl)-2-azabicyclo[2.2.1]heptan-3-one (8) is made by a process described herein. Methyl (S)-3-((tert-Butoxycarbonyl)amino)-4-(difluoromethylene)cyclopent-1-ene-1-carboxylate (9) is provided herein. Compositions including methyl (S)-3-((tert-butoxycarbonyl)amino)-4-(difluoromethylene)cyclopent-1-ene-1-carboxylate (9) are provided herein. Pharmaceutical compositions including methyl (S)-3-((tert-butoxycarbonyl)amino)-4-(difluoromethylene)cyclopent-1-ene-1-carboxylate (9) are provided herein. Methyl (S)-3-((tert-Butoxycarbonyl)amino)-4-(difluoromethylene)cyclopent-1-ene-1-carboxylate (9) is made by a process described herein.

Compositions including (S)-3-amino-4-(difluoromethylenyl)cyclopent-1-ene-1-carboxylic acid (1) and (1S,3S)-3-amino-4-(difluoromethylidene)cyclopentane-1-carboxylic acid are provided. Pharmaceutical compositions including (S)-3-amino-4-(difluoromethylenyl)cyclopent-1-ene-1-carboxylic acid (1) and (1S,3S)-3-amino-4-(difluoromethylidene)cyclopentane-1-carboxylic acid are provided.

Compositions including (S)-3-amino-4-(difluoromethylenyl)cyclopent-1-ene-1-carboxylic acid (1) and one or more of (1R,4S)-2-Azabicyclo[2.2.1]hept-5-en-3-one (2), (1R,4S)-2-(4-methoxybenzyl)-2-azabicyclo[2.2.1]hept-5-en-3- one (3), (1R,4R,6S,7R)-7-bromo-2-(4-methoxybenzyl)-3-oxo-2-azabicyclo[2.2.1]heptan-6-yl acetate (4), (1R,4R,6S,7R)-7-bromo-6-hydroxy-2-(4-methoxybenzyl)-2-azabicyclo[2.2.1]heptan-3-one (25), (1R,4R,7R)-7-bromo-2-(4-methoxybenzyl)-2-azabicyclo[2.2.1]heptane-3,6-dione (5), (1R,4R,7R)-7-bromo-6-(difluoromethylene)-2-azabicyclo[2.2.1]heptan-3-one (6), (1R,4R,7R)-7-bromo-6-(difluoromethylene)-2-azabicyclo[2.2.1]heptan-3-one (7), (1R,4R,7R)-7-bromo-6-(difluoromethylene)-2-(tert-butoxycarbonyl)-2-azabicyclo[2.2.1]heptan-3-one (8), (S)-3-((Tert-butoxycarbonyl)amino)-4-(difluoromethylene)cyclopent-1-ene-1-carboxylic acid (19), or methyl (S)-3-((tert-butoxycarbonyl)amino)-4-(difluoromethylene)cyclopent-1-ene-1-carboxylate (9) are provided.

A process for preparing (S)-3-amino-4-(difluoromethylenyl)cyclopent-1-ene-1-carboxylic acid (1) is provided which includes converting ethyl-cyclopent-3-ene-carboxylate (10) to (3R,4S)-ethyl-3-((tert-butoxycarbonyl)amino)-4-(hydroxy)cyclopentane carboxylate (11). (3R,4S)-Ethyl-3-((tert-butoxycarbonyl)amino)-4-(hydroxy)cyclopentane carboxylate (11) is converted to (3R)-ethyl-3-((tert-butoxycarbonyl)amino)-4-oxo-cyclopentane carboxylate (12). (3R)-Ethyl-3-((tert-butoxycarbonyl)amino)-4-oxo-cyclopentane carboxylate is converted to ethyl (9S)-9-(tert-butoxycarbonylamino)-1,4-dioxa-7-spiro[4.4]nonanecarboxylate (13). Ethyl (9S)-9-(tert-butoxycarbonylamino)-1,4-dioxa-7-spiro[4.4]nonanecarboxylate (13) is converted to ethyl (S)-9-(tert-butoxycarbonylamino)-1,4-dioxa-7-spiro[4.4]nonene-7-carboxylate (14). Ethyl (S)-9-(tert-butoxycarbonylamino)-1,4-dioxa-7-spiro[4.4]nonene-7-carboxylate (14) is converted to ethyl (S)-3-((tert-butoxycarbonyl)amino)-4-(difluoromethylene)cyclopent-1-ene-1-carboxylate (15). Ethyl (S)-3-((tert-butoxycarbonyl)amino)-4-(difluoromethylene)cyclopent-1-ene-1-carboxylate (15) is converted to (S)-3-amino-4-(difluoromethylenyl)cyclopent-1-ene-1-carboxylic acid (1).

(3R,4S)-Ethyl-3-((tert-butoxycarbonyl)amino)-4-(hydroxy)cyclopentane carboxylate (11) is provided herein. Compositions including (3R,4S)-ethyl-3-((tert-butoxycarbonyl)amino)-4-(hydroxy)cyclopentane carboxylate (11) are provided herein. Pharmaceutical compositions including (3R,4S)-ethyl-3-((tert-butoxycarbonyl)amino)-4-(hydroxy)cyclopentane carboxylate (11) are provided herein. (3R,4S)-Ethyl-3-((tert-butoxycarbonyl)amino)-4-(hydroxy)cyclopentane carboxylate (11) is made by a process described herein.

(3R)-Ethyl-3-((tert-butoxycarbonyl)amino)-4-oxo-cyclopentane carboxylate (12) is provided herein. Compositions including (3R)-ethyl-3-((tert-butoxycarbonyl)amino)-4-oxo-cyclopentane carboxylate (12) are provided herein. Pharmaceutical compositions including (3R)-ethyl-3-((tert-butoxycarbonyl)amino)-4-oxo-cyclopentane carboxylate (12) are provided herein. (3R)-Ethyl-3-((tert-butoxycarbonyl)amino)-4-oxo-cyclopentane carboxylate (12) is made by a process described herein.

Ethyl (9S)-9-(tert-butoxycarbonylamino)-1,4-dioxa-7-spiro[4.4]nonanecarboxylate (13) is provided herein. Compositions including ethyl (9S)-9-(tert-butoxycarbonylamino)-1,4-dioxa-7-spiro[4.4]nonanecarboxylate (13) are provided herein. Pharmaceutical compositions including ethyl (9S)-9-(tert-butoxycarbonylamino)-1,4-dioxa-7-spiro[4.4]nonanecarboxylate (13) are provided herein. Ethyl (9S)-9-(tert-butoxycarbonylamino)-1,4-dioxa-7-spiro[4.4]nonanecarboxylate (13) is made by a process described herein.

Ethyl (S)-9-(tert-butoxycarbonylamino)-1,4-dioxa-7-spiro[4.4]nonene-7-carboxylate (14) is provided herein.

Compositions including ethyl (S)-9-(tert-butoxycarbonylamino)-1,4-dioxa-7-spiro[4.4]nonene-7-carboxylate (14) are provided herein. Pharmaceutical compositions including ethyl (S)-9-(tert-butoxycarbonylamino)-1,4-dioxa-7-spiro[4.4]nonene-7-carboxylate (14) are provided herein. Ethyl (S)-9-(tert-butoxycarbonylamino)-1,4-dioxa-7-spiro[4.4]nonene-7-carboxylate (14) is made by a process described herein.

Ethyl (S)-3-((tert-butoxycarbonyl)amino)-4-(difluoromethylene)cyclopent-1-ene-1-carboxylate (15) is provided herein. Compositions including ethyl (S)-3-((tert-butoxycarbonyl)amino)-4-(difluoromethylene)cyclopent-1-ene-1-carboxylate (15) are provided herein. Pharmaceutical compositions including ethyl (S)-3-((tert-butoxycarbonyl)amino)-4-(difluoromethylene)cyclopent-1-ene-1-carboxylate (15) are provided herein. Ethyl (S)-3-((tert-butoxycarbonyl)amino)-4-(difluoromethylene)cyclopent-1-ene-1-carboxylate (15) is made by a process described herein.

Compositions including (S)-3-amino-4-(difluoromethylenyl)cyclopent-1-ene-1-carboxylic acid (1) and one or more of ethyl-cyclopent-3-ene-carboxylate (10), (3R,4S)-ethyl-3-((tert-butoxycarbonyl)amino)-4-(hydroxy)cyclopentane carboxylate (11), (3R)-ethyl-3-((tert-butoxycarbonyl)amino)-4-oxo-cyclopentane carboxylate (12), ethyl (9S)-9-(tert-butoxycarbonylamino)-1,4-dioxa-7-spiro[4.4]nonanecarboxylate (13), ethyl (S)-9-(tert-butoxycarbonylamino)-1,4-dioxa-7-spiro[4.4]nonene-7-carboxylate (14), or ethyl (S)-3-((tert-butoxycarbonyl)amino)-4-(difluoromethylene)cyclopent-1-ene-1-carboxylate (15), are provided

DETAILED DESCRIPTION

Figure 1:
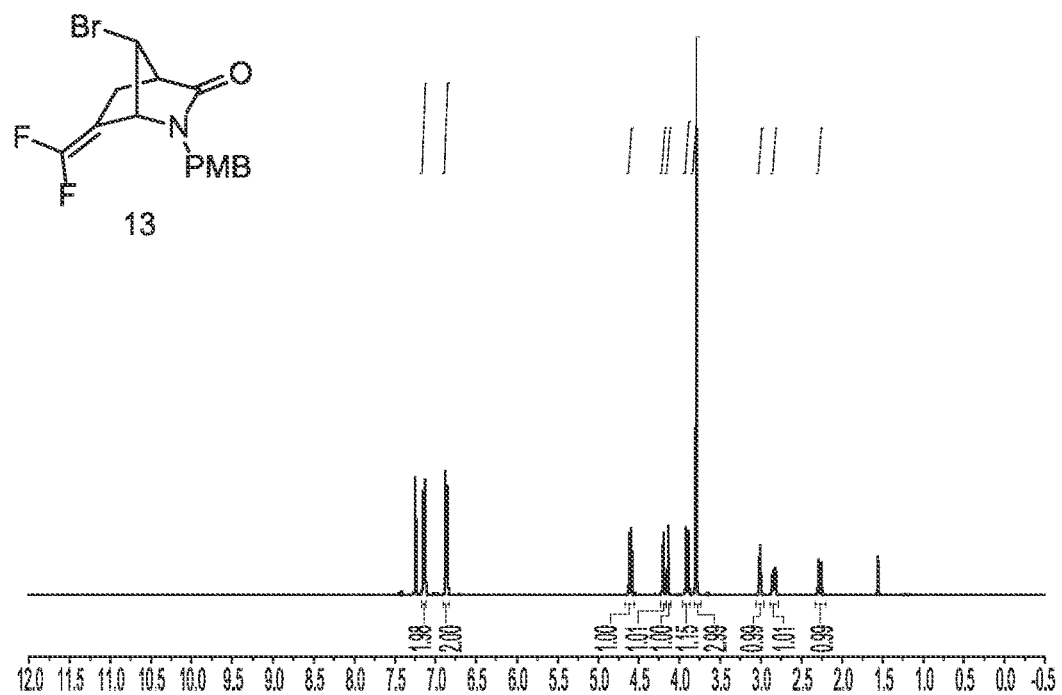
FIG. 1 is a 500 MHz $^1$H NMR spectrum (CDCl$_3$) of (1R,4R,7R)-7-bromo-6-(difluoromethylene)-2-(4-methoxybenzyl)-2-azabicyclo[2.2.1]heptan-3-one (6).

Provided herein are processes, compounds and compositions for making (S)-3-amino-4-(difluoromethylenyl)cyclopent-1-ene-1-carboxylic acid (1). The processes herein are scalable and high yielding as compared to the existing technique, avoid the use of selenium and tert-butyllithium, and avoid forming multiple isomers from an α-elimination. In embodiments, the present process incorporates elimination of a leaving group from the β-position, precludes a resulting mixture of isomers, reduces the number of synthesis steps from fourteen to nine as compared to the existing technique, and increases yield from 3.7% to 8.1%.

In embodiments, synthesis of (S)-3-amino-4-(difluoromethylenyl)cyclopent-1-ene-1-carboxylic acid (1) is shown in Scheme 1 starting with ((1R,4S)-2-azabicyclo[2.2.1]hept-5-en-3-one) (2).

bromo-2-(4-methoxybenzyl)-3-oxo-2-azabicyclo[2.2.1]heptan-6-yl acetate (4). (1R,4R,6S,7R)-7-Bromo-2-(4-methoxybenzyl)-3-oxo-2-azabicyclo[2.2.1]heptan-6-yl acetate (4) is converted to (1R,4R,7R)-7-bromo-2-(4-methoxybenzyl)-2-azabicyclo[2.2.1]heptane-3,6-dione (5). (1R,4R,7R)-7-Bromo-2-(4-methoxybenzyl)-2-azabicyclo[2.2.1]heptane-3,6-dione (5) is converted to (1R,4R,7R)-7-bromo-6-(difluoromethylene)-2-(4-methoxybenzyl)-2-azabicyclo[2.2.1]heptan-3-one (6). (1R,4R,7R)-7-Bromo-6-(difluoromethylene)-2-(4-methoxybenzyl)-2-azabicyclo[2.2.1]heptan-3-one (6) is converted to (1R,4R,7R)-7-bromo-6-(difluoromethylene)-2-azabicyclo[2.2.1]heptan-3-one (7). (1R,4R,7R)-7-Bromo-6-(difluoromethylene)-2-azabicyclo[2.2.1]heptan-3-one (7) is converted to (1R,4R,7R)-7-bromo-6-(difluoromethylene)-2-(tert-butoxycarbonyl)-2-azabicyclo[2.2.1]heptan-3-one (8). (1R,4R,7R)-7-Bromo-6-(difluoromethylene)-2-(tert-butoxycarbonyl)-2-azabicyclo[2.2.1]heptan-3-one (8) is converted to methyl (S)-3-((tert-butoxycarbonyl)amino)-4-(difluoromethylene)cyclopent-1-ene-1-carboxylate (9).

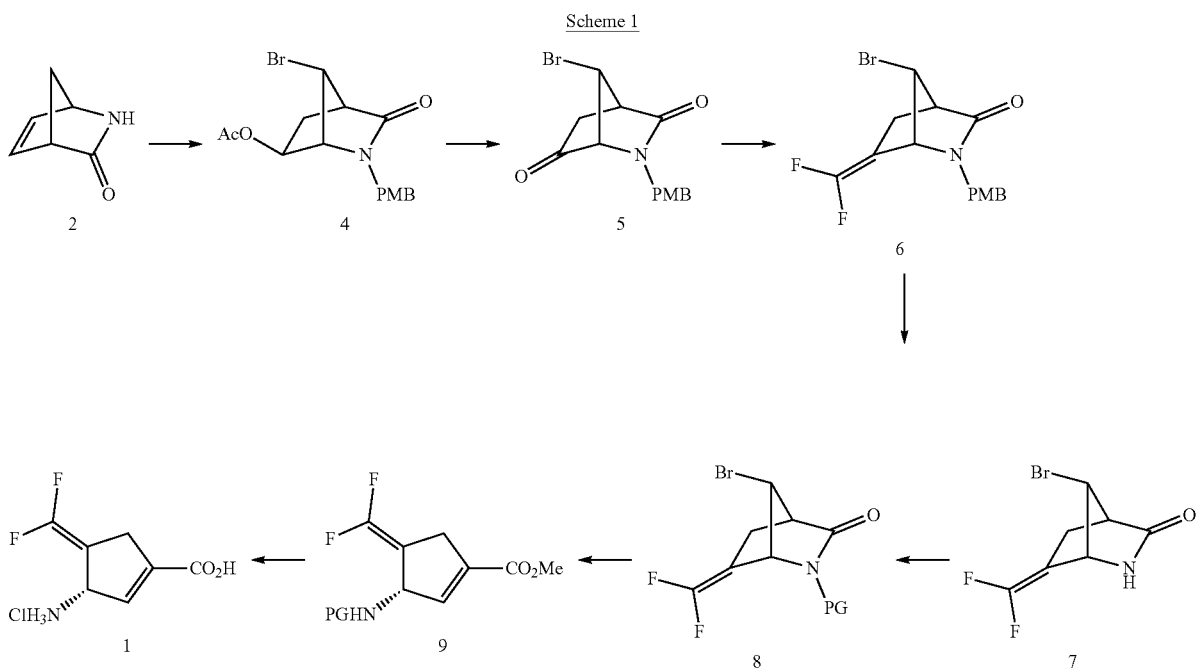

Scheme 1

AC = Acetyl, PMB = 4-Methoxybenzyl, PG = Protecting Group

According to Scheme 1, a process for preparing (S)-3-amino-4-(difluoromethylenyl)cyclopent-1-ene-1-carboxylic acid (1) or salt thereof is provided which includes converting ((1R,4S)-2-azabicyclo[2.2.1]hept-5-en-3-one) (2) to (1R,4S)-2-(4-methoxybenzyl)-2-azabicyclo[2.2.1]hept-5-en-3-one (3). (1R,4S)-2-(4-Methoxybenzyl)-2-azabicyclo[2.2.1]hept-5-en-3-one (3) is converted to (1R,4R,6S,7R)-7-

Methyl (S)-3-((tert-butoxycarbonyl)amino)-4-(difluoromethylene)cyclopent-1-ene-1-carboxylate (9) is converted to (S)-3-amino-4-(difluoromethylenyl)cyclopent-1-ene-1-carboxylic acid (1).

In embodiments, synthesis of (S)-3-amino-4-(difluoromethylenyl)cyclopent-1-ene-1-carboxylic acid (1) is shown in Scheme 1A.

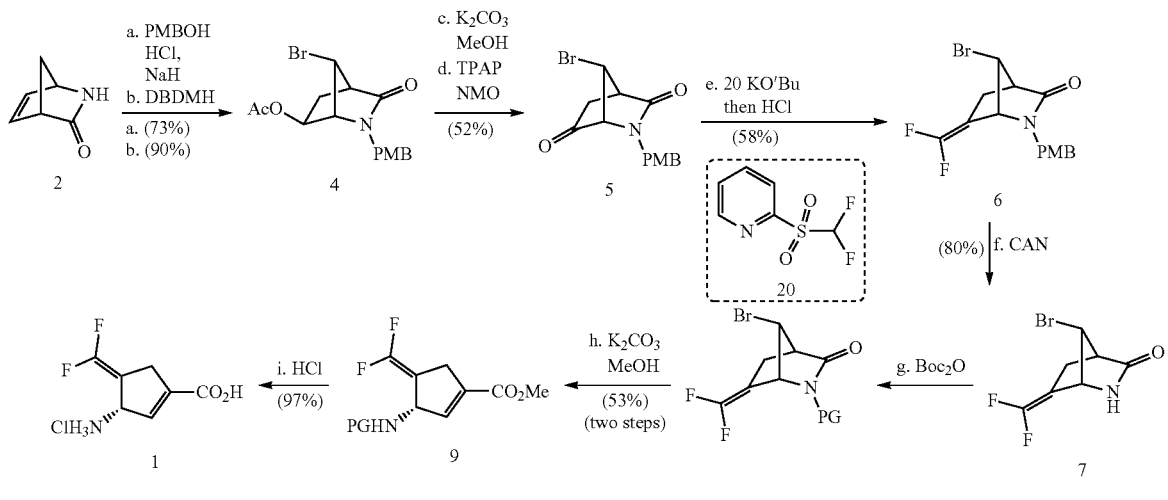

Abbreviations: PMBOH: 4-methoxybenzyl alcohol; DMF: N-N-dimethylformamide; DBDMH: 1,3-dibromo-5,5-dimethylhydantoin; TPAP: tetrapropylammonium perruthenate; NMO: N-methylmorpholine N-oxide; CAN: ceric ammonium nitrite; DMAP: N,N-dimethylaminopyridine In embodiments, starting from ((1R,4S)-2-azabicyclo[2.2.1]hept-5-en-3-one) (2) (also known as the Vince lactam) and following a modification of literature steps such as the use of PMBOH/HCl, (See, Qiu, J.; Silverman, R. B. J. Med. Chem. 2000, 43, 706-720), (1R,4R,6S,7R)-7-bromo-2-(4-methoxybenzyl)-3-oxo-2-azabicyclo[2.2.1]heptan-6-yl acetate (4) is obtained on a multi-gram scale (Scheme 1A): a. PMBOH, HCl, NaH, THF/DMF; b. DBDMH, AcOH.

Alcoholysis of the acetate and oxidation yields ketone (1R,4R,7R)-7-bromo-2-(4-methoxybenzyl)-2-azabicyclo[2.2.1]heptane-3,6-dione (5): c. $K_2CO_3$, alcohol; d. TPAP, NMO, 4 Å MS, $CH_2Cl_2$, over two steps. The foregoing allows difluoro-Horner-Wadsworth-Emmons olefination of ketone 5. When 2-((difluoromethyl)sulfinyl)pyridine (20) (also known as Hu's reagent) is employed with KO$^t$Bu as base, (1R,4R,7R)-7-bromo-6-(difluoromethylene)-2-(4-methoxybenzyl)-2-azabicyclo[2.2.1]heptan-3-one (6) is obtained: e. 2-((difluoromethyl)sulfinyl)pyridine (20), KO$^t$Bu, DMF, then NH4Cl, then HCl. Alternatively, e. can be tert-BuLi and $F_2$CHP(O)(OEt)$_2$ (See, Pan, Y.; Qiu, J.; Silverman, R. B. J. Med. Chem. 2003, 46, 5292-5293). The next step is alcoholysis of the lactam and elimination. (1R,4R,7R)-7-Bromo-6-(difluoromethylene)-2-(4-methoxybenzyl)-2-azabicyclo[2.2.1]heptan-3-one (6) is deprotected to yield (1R,4R,7R)-7-bromo-6-(difluoromethylene)-2-azabicyclo[2.2.1]heptan-3-one (7): f. CAN, MeCN, $H_2O$. A small amount of 4-methoxybenzoyl protected lactam may also be isolated. Boc protection of the lactam (1R,4R,7R)-7-bromo-6-(difluoromethylene)-2-azabicyclo[2.2.1]heptan-3-one) (7) yields (1R,4R,7R)-7-bromo-6-(difluoromethylene)-2-(tert-butoxycarbonyl)-2-azabicyclo[2.2.1]heptan-3-one (8): g. Boc$_2$O, DMAP, Et$_3$N, CH$_2$Cl$_2$.

Alcoholysis of (1R,4R,7R)-7-bromo-6-(difluoromethylene)-2-(tert-butoxycarbonyl)-2-azabicyclo[2.2.1]heptan-3-one (8) with $K_2CO_3$ and alcohol, leads to subsequent elimination of the bromide to yield methyl or ethyl (S)-3-((tert-butoxycarbonyl)amino)-4-(difluoromethylene)cyclopent-1-ene-1-carboxylate (9): h. $K_2CO_3$, alcohol, over two steps. Final deprotection in HCl yields (S)-3-amino-4-(difluoromethylenyl)cyclopent-1-ene-1-carboxylic acid (1) with no observable isomerization or degradation: i. HCl, dioxane. Although methanol is shown in the above schematic, it should be understood that alcohols such as ethanol or propanol may be utilized as an alcohol.

In embodiments, starting from ((1R,4S)-2-azabicyclo[2.2.1]hept-5.-en-3-one) (2) (Vince lactam) and following a modification of literature steps (see, Qiu et al. supra), e.g., use of PMBOH/HCl, (1R,4R,6S,7R)-7-bromo-2-(4-methoxybenzyl)-3-oxo-2-azabicyclo[2.2.1]heptan-6-yl acetate (4) is obtained on a multi-gram scale (Scheme 1A): a. PMBOH (1-2 equiv.), HCl, NaH (0.8-1.5 equiv.) 0-5° C., THF/DMF (0.75-1.5:0.75-1.5), 4-8 h; b. DBDMH (0.4-0.8 equiv), AcOH, 15-30° C., 4-8 h; Methanolysis of the acetate and oxidation yields ketone (1R,4R,7R)-7-bromo-2-(4-methoxybenzyl)-2-azabicyclo[2.2.1]heptane-3,6-dione (5): c. $K_2CO_3$ (2-4 equiv), MeOH 0.5-2 h; d. TPAP (0.001-0.2 equiv), NMO (1.0-3.0 equiv), 4 Å MS, CH$_2$Cl$_2$, 15-25 h, over two steps. The foregoing allows difluoro-Horner-Wadsworth-Emmons olefination of ketone 5. When 2-((difluoromethyl)sulfinyl)pyridine (20) (Hu's reagent) is employed with KO$^t$Bu as base, (1R,4R,7R)-7-bromo-6-(difluoromethylene)-2-(4-methoxybenzyl)-2-azabicyclo[2.2.1]heptan-3-one (6) is obtained, e.g., infusion of base over 15 minutes to 2 hours with NH$_4$Cl/6 M HCl quench: e. 2-((difluoromethyl)sulfinyl)pyridine (20) (1.0-1.5 equiv), KO$^t$Bu (1.25-1.75 equiv), DMF,-80-–40° C., 15-60 min, then NH4Cl, then HCl, then 15-30° C., then 40-80° C., 1 h. Alternatively, e. can be tert-BuLi and F$_2$CHP(O)(OEt)$_2$ (See, Pan, Y. et al. supra). The next step is methanolysis of the lactam and elimination. (1R,4R,7R)-7-Bromo-6-(difluoromethylene)-2-(4-methoxybenzyl)-2-azabicyclo[2.2.1]heptan-3-one (6) is deprotected to yield (1R,4R,7R)-7-bromo-6-(difluoromethylene)-2-azabicyclo[2.2.1]heptan-3-one (7): f. CAN (2-4 equiv), MeCN, H$_2$O, –10 to 10° C., 0.75-2 h. A small amount of 4-methoxybenzoyl protected lactam may also be isolated. Boc protection of the lactam (1R,4R,7R)-7-bromo-6-(difluoromethylene)-2-azabicyclo[2.2.1]heptan-3-one) (7) yields (1R,4R,7R)-7-bromo-6-(difluoromethylene)-2-(tert-butoxycarbonyl)-2-azabicyclo[2.2.1]heptan-3-one (8): g. Boc$_2$O (1.0-1.5 equiv), DMAP (0.01-0.5 equiv), Et$_3$N (1.0-2.0 equiv), CH$_2$Cl$_2$, 0.5-2.0 h. Methanolysis of (1R,4R,7R)-7-bromo-6-(difluoromethylene)-2-(tert-butoxycarbonyl)-2-azabicyclo[2.2.1]heptan-3-one (8) with $K_2CO_3$ and methanol, leads to subsequent elimination of the bromide to yield methyl (S)-3-((tert-butoxycarbonyl)amino)-4-(difluoromethylene)cyclopent-1-ene-1-carboxylate (9): h. $K_2CO_3$ (2-4 equiv), MeOH, 4-8 h, over two steps. Final deprotection at 70-90° C. in 6M HCl yields (S)-3-amino-4-(difluoromethylenyl)cyclopent-1-ene-1-carboxylic acid (1) with no observable isomerization or degradation: i. HCl (6 M), dioxane, 70-90° C., 1-3 h.

In embodiments, starting from ((1R,4S)-2-azabicyclo[2.2.1]hept-5-en-3-one) (2) (Vince lactam) and following a modification of literature steps such as the use of PMBOH/HCl, (See, Qiu, J., eta al. supra), (1R,4R,6S,7R)-7-bromo-2-(4-methoxybenzyl)-3-oxo-2-azabicyclo[2.2.1]heptan-6-yl acetate (4) is obtained on a multi-gram scale (Scheme 1A): a. PMBOH (1.5 equiv.), HCl, NaH (1.1 equiv.) 0° C., THF/DMF (1:1), 6 h, 73%; b. DBDMH (0.6 equiv), AcOH, 23° C., 6 h, 90%; Methanolysis of the acetate and oxidation yields ketone (1R,4R,7R)-7-bromo-2-(4-methoxybenzyl)-2-azabicyclo[2.2.1]heptane-3,6-dione (5): c. $K_2CO_3$ (3 equiv), MeOH 1 h; d. TPAP (0.01 equiv), NMO (2.0 equiv), 4 Å MS, $CH2Cl_2$, 18 h, 52% over two steps. The foregoing provides a modality to run these steps on multi-gram scale allowing difluoro-Horner-Wadsworth-Emmons olefination of ketone 5. When 2-((difluoromethyl)sulfinyl)pyridine (20) (Hu's reagent) is employed with $KO^tBu$ as base, employing Hu's reported conditions (see, Zhao, Y.; Huang, W.; Zhu, L.; Hu, J. Org. Lett. 2010, 12, 1444-1447), (1R,4R,7R)-7-bromo-6-(difluoromethylene)-2-(4-methoxybenzyl)-2-azabicyclo[2.2.1]heptan-3-one (6) is obtained in small amounts (<10% yield). Slow infusion of base over 30 minutes with $NH_4Cl$/6 M HCl quench dramatically increases the yield to 45%. Prolonging infusion of base to one hour increases the yield to 58%. See, Table 1, below. The reaction was not greatly affected by scale, allowing scale up to 3.5 g of (1R,4R,7R)-7-bromo-2-(4-methoxybenzyl)-2-azabicyclo[2.2.1]heptane-3,6-dione (5) with no decrease in yield: e. 2-((difluoromethyl)sulfinyl)pyridine (20) (1.2 equiv), $KO^tBu$ (1.5 equiv), DMF, –60° C., 30 min, then NH4Cl, then 6 M HCl, then 23° C., then 60° C., 1 h. Alternatively, e. can be tert-BuLi and $F_2CHP(O)(OEt)_2$ (See, Pan, et al., supra). The next step is methanolysis of the lactam and elimination. (1R,4R,7R)-7-Bromo-6-(difluoromethylene)-2-(4-methoxybenzyl)-2-azabicyclo[2.2.1]heptan-3-one (6) is deprotected to yield (1R,4R,7R)-7-bromo-6-(difluoromethylene)-2-azabicyclo[2.2.1]heptan-3-one (7) in 80% yield: f. CAN (3 equiv), MeCN, $H_2O$, 0° C., 1 h. A small amount of 4-methoxybenzoyl protected lactam may also be isolated. Boc protection of the lactam (1R,4R,7R)-7-bromo-6-(difluoromethylene)-2-azabicyclo[2.2.1]heptan-3-one) (7) yields (1R,4R,7R)-7-bromo-6-(difluoromethylene)-2-(tert-butoxycarbonyl)-2-azabicyclo[2.2.1]heptan-3-one (8): g. $Boc_2O$ (1.2 equiv), DMAP (0.1 equiv), $Et_3N$ (1.5 equiv), $CH_2Cl_2$, 1 h. Methanolysis of (1R,4R,7R)-7-bromo-6-(difluoromethylene)-2-(tert-butoxycarbonyl)-2-azabicyclo[2.2.1]heptan-3-one (8) with $K_2CO_3$ and methanol, leads to subsequent elimination of the bromide to yield methyl (S)-3-((tert-butoxycarbonyl)amino)-4-(difluoromethylene)cyclopent-1-ene-1-carboxylate (9): h. $K_2CO_3$ (3 equiv), MeOH, 6 h, 52% over two steps. Final deprotection at 80° C. in 6M HCl yields (S)-3-amino-4-(difluoromethylenyl)cyclopent-1-ene-1-carboxylic acid (1) in 97% yield with no observable isomerization or degradation: i. HCl (6 M), dioxane, 80° C., 2 h. Overall, the yield from Vince Lactam (2) to S)-3-amino-4-(difluoromethylene)cyclopent-1-ene-1-carboxylic acid (1) is 8.1%.

TABLE 1

Optimization of Fluorination[a]

| entry | scale (g) | base addition method | quench (time)[b] | yield[c] |
|---|---|---|---|---|
| 1 | 0.05 | dropwise over 5 min | 6M HCl (5 min) | 0 |
| 2 | 0.05 | dropwise over 5 min | 6M HCl (1 h) | 9% |
| 3 | 0.05 | dropwise over 5 min | a. sat. $NH_4Cl$ (1 h) b. 6M HCl (1 min) | 15% |
| 4 | 0.13 | infusion over 30 min | a. sat. $NH_4Cl$ (1 h) b. 6M HCl (2 min) | 45% |
| 5 | 1 | infusion over 60 min | a. sat. $NH_4Cl$ (1 h) b. 6M HCl (2 min) | 58% |
| 6 | 3.5 | infusion over 90 min | a. sat. $NH_4Cl$ (1 h) b. 6M hCl (2 min) | 50% |

[a]Conditions: 5 (1 equiv), 20 (1.2 equiv), DMF (0.3M) –60° C., then $KO^tBu$ (1.5 equiv) in DMF (0.5M), then quench at –60° C., then 23° C., then 60° C. for 1 h;
[b]time before quenching solution was added;
[c]isolated yield after chromatography.

In embodiments, without wishing to be bound by any theory, the following is a proposed mechanism for fluorination of (1R,4R,7R)-7-Bromo-2-(4-methoxybenzyl)-2-azabicyclo[2.2.1]heptane-3,6-dione (5):

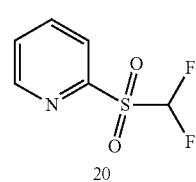

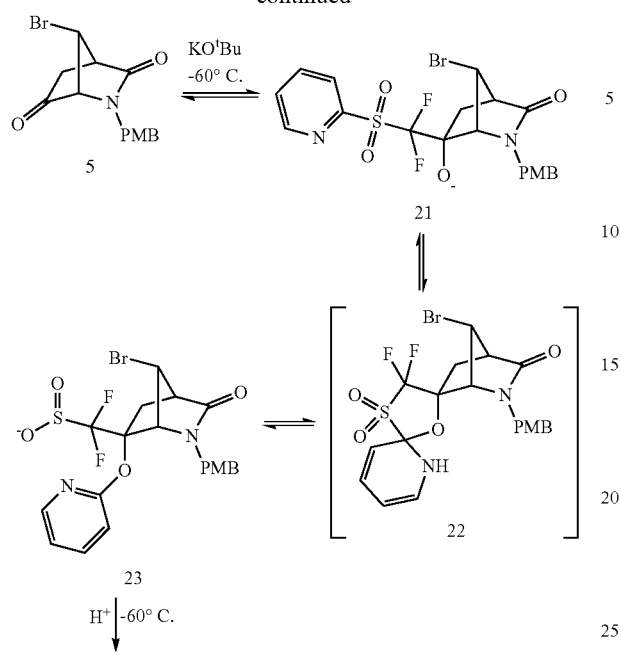

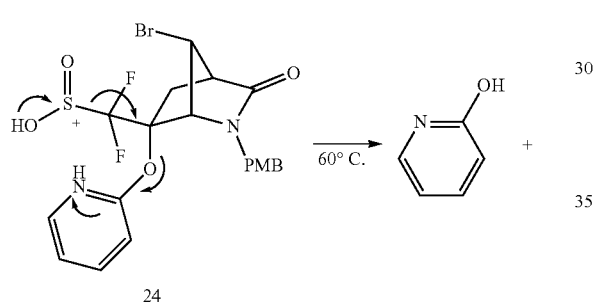

As shown above, multiple intermediates form during the course of the fluorination reaction. Intermediate 21, which forms first, rearranges via cyclic intermediate 22 to form sulfonate 23, which is then protonated, triggering elimination and formation of the olefin (see above). If the reaction were quenched at −60° C. with 6 M HCl five minutes after the addition of KO$^t$Bu to a mixture of 5 and 20, then only 21 was observed by LC/MS (entry 1, Table 1). Addition of KO$^t$Bu followed by a 6 M HCl quench at −60° C. (entry 2, Table 1), and subsequent heating at 60° C. for 1 h provided 6 in 9% yield along with starting material and intermediate 21. Quenching after 1 hour with a saturated NH4Cl solution, followed by 6 M HCl, slightly improved the yield (entry 3, Table 1). Slow infusion of base with a syringe pump over 30 min with an NH$_4$Cl/6 M HCl quench dramatically increased the yield to 45%. Prolonging infusion of base to one hour increased the yield to 58%.

In embodiments, the following compounds are provided:

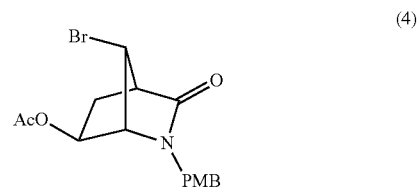

(1R,4R,6S,7R)-7-Bromo-2-(4-methoxybenzyl)-3-oxo-2-azabicyclo[2.2.1]heptan-6-yl acetate (4)

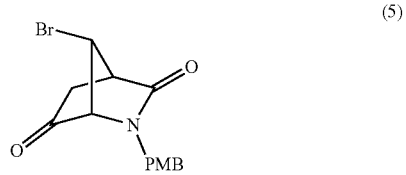

(1R,4R,7R)-7-Bromo-2-(4-methoxybenzyl)-2-azabicyclo[2.2.1]heptane-3,6-dione (5)

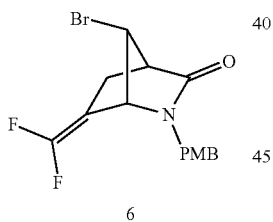

(1R,4R,7R)-7-Bromo-6-(difluoromethylene)-2-(4-methoxybenzyl)-2-azabicyclo[2.2.1]heptan-3-one (6)

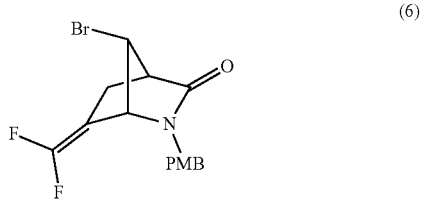

(1R,4R,7R)-7-Bromo-6-(difluoromethylene)-2-azabicyclo[2.2.1]heptan-3-one (7)

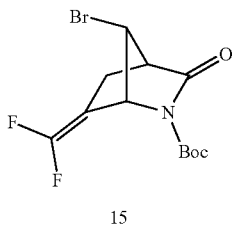

(1R,4R,7R)-7-Bromo-6-(difluoromethylene)-2-(tert-butoxycarbonyl)-2-azabicyclo[2.2.1]heptan-3-one (8)

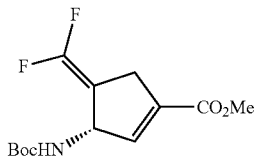

Methyl (S)-3-((tert-butoxycarbonyl)amino)-4-(difluoromethylene)cyclopent-1-ene-1-carboxylate (9)

In embodiments, compositions including (1R,4S)-2-(4-methoxybenzyl)-2-azabicyclo[2.2.1]hept-5-en-3-one (3) or a salt thereof are provided herein. Such compositions may include reaction mixtures such as those described herein. Compositions including (1R,4S)-2-(4-methoxybenzyl)-2-azabicyclo[2.2.1]hept-5-en-3-one (3) or a salt thereof may include polar solvents, e.g., aqueous, methanol, ethanol, DMF, acetic acid, etc. or non-polar solvents, e.g., diethyl ether, hexane, dichloromethane, ethyl acetate, etc. Compositions including (1R,4S)-2-(4-methoxybenzyl)-2-azabicyclo[2.2.1]hept-5-en-3-one (3) or a pharmaceutically acceptable salt thereof can be pharmaceutical compositions. Compositions can include (1R,4S)-2-(4-methoxybenzyl)-2-azabicyclo[2.2.1]hept-5-en-3-one (3) or a salt thereof in amounts of from 0.0001 mg to 50 mg or more. For example, a pharmaceutical composition may include (1R,4S)-2-(4-methoxybenzyl)-2-azabicyclo[2.2.1]hept-5-en-3-one (3) or a pharmaceutically acceptable salt thereof in amounts greater than 0.0001 mg, e.g., from 0.0001 mg to 0.0002 mg, 0.0001 mg to 0.0003 mg, 0.0002 mg to 0.0003 mg, 0.0003 mg to 0.0004 mg, 0.0004 mg to 0.0005 mg, 0.0005 mg to 0.0006 mg, 0.0006 mg to 0.0007 mg, 0.0007 mg to 0.0008 mg, 0.0008 mg to 0.0009 mg, 0.0009 mg to 0.001 mg, 0.001 mg to 0.002 mg, 0.002 mg to 0.003 mg, 0.003 mg to 0.004 mg, 0.004 mg to 0.005 mg, 0.005 mg to 0.006 mg, 0.006 mg to 0.007 mg, 0.007 mg to 0.008 mg, 0.008 mg to 0.009 mg, 0.009 mg to 0.01 mg, 0.01 mg to 0.02 mg, 0.02 mg to 0.03 mg, 0.03 mg to 0.04 mg, 0.04 mg to 0.05 mg, 0.05 mg to 0.06 mg, 0.06 mg to 0.07 mg, 0.07 mg to 0.08 mg, 0.08 mg to 0.09 mg, 0.09 mg to 0.1 mg, 0.1 mg to 0.2 mg, 0.2 mg to 0.3 mg, 0.3 mg to 0.4 mg, 0.4 mg to 0.5 mg, 0.5 mg to 0.6 mg, 0.6 mg to 0.7 mg, 0.7 mg to 0.8 mg, 0.8 mg to 0.9 mg, 0.9 mg to 1.0 mg, 1.0 mg to 2.0 mg, 2.0 mg to 3.0 mg, 3.0 mg to 4.0 mg, 4.0 mg to 5.0 mg, 5.0 mg to 6.0 mg, 6.0 mg to 7.0 mg, 7.0 mg to 8.0 mg, 8.0 mg to 9.0 mg, or 9.0 mg to 10 mg.

In embodiments, compositions including (1R,4R,6S,7R)-7-bromo-2-(4-methoxybenzyl)-3-oxo-2-azabicyclo[2.2.1]heptan-6-yl acetate (4) or a salt thereof are provided herein. Such compositions may include reaction mixtures such as those described herein. Compositions including (1R,4R,6S,7R)-7-bromo-2-(4-methoxybenzyl)-3-oxo-2-azabicyclo[2.2.1]heptan-6-yl acetate (4) or a salt thereof may include polar solvents, e.g., aqueous, methanol, ethanol, DMF, acetic acid, etc. or non-polar solvents, e.g., diethyl ether, hexane, dichloromethane, ethyl acetate, etc. Compositions including (1R,4R,6S,7R)-7-bromo-2-(4-methoxybenzyl)-3-oxo-2-azabicyclo[2.2.1]heptan-6-yl acetate (4) or a pharmaceutically acceptable salt thereof can be pharmaceutical compositions. Compositions can include (1R,4R,6S,7R)-7-bromo-2-(4-methoxybenzyl)-3-oxo-2-azabicyclo[2.2.1]heptan-6-yl acetate (4) or a salt thereof in amounts of from 0.0001 mg to 50 mg or more. For example, a pharmaceutical composition may include (1R,4R,6S,7R)-7-bromo-2-(4-methoxybenzyl)-3-oxo-2-azabicyclo[2.2.1]heptan-6-yl acetate (4) or a pharmaceutically acceptable salt thereof in amounts greater than 0.0001 mg, e.g., from 0.0001 mg to 0.0002 mg, 0.0001 mg to 0.0003 mg, 0.0002 mg to 0.0003 mg, 0.0003 mg to 0.0004 mg, 0.0004 mg to 0.0005 mg, 0.0005 mg to 0.0006 mg, 0.0006 mg to 0.0007 mg, 0.0007 mg to 0.0008 mg, 0.0008 mg to 0.0009 mg, 0.0009 mg to 0.001 mg, 0.001 mg to 0.002 mg, 0.002 mg to 0.003 mg, 0.003 mg to 0.004 mg, 0.004 mg to 0.005 mg, 0.005 mg to 0.006 mg, 0.006 mg to 0.007 mg, 0.007 mg to 0.008 mg, 0.008 mg to 0.009 mg, 0.009 mg to 0.01 mg, 0.01 mg to 0.02 mg, 0.02 mg to 0.03 mg, 0.03 mg to 0.04 mg, 0.04 mg to 0.05 mg, 0.05 mg to 0.06 mg, 0.06 mg to 0.07 mg, 0.07 mg to 0.08 mg, 0.08 mg to 0.09 mg, 0.09 mg to 0.1 mg, 0.1 mg to 0.2 mg, 0.2 mg to 0.3 mg, 0.3 mg to 0.4 mg, 0.4 mg to 0.5 mg, 0.5 mg to 0.6 mg, 0.6 mg to 0.7 mg, 0.7 mg to 0.8 mg, 0.8 mg to 0.9 mg, 0.9 mg to 1.0 mg, 1.0 mg to 2.0 mg, 2.0 mg to 3.0 mg, 3.0 mg to 4.0 mg, 4.0 mg to 5.0 mg, 5.0 mg to 6.0 mg, 6.0 mg to 7.0 mg, 7.0 mg to 8.0 mg, 8.0 mg to 9.0 mg, or 9.0 mg to 10 mg.

In embodiments, compositions including (1R,4R,7R)-7-bromo-2-(4-methoxybenzyl)-2-azabicyclo[2.2.1]heptane-3,6-dione (5) or a salt thereof are provided herein. Such compositions may include reaction mixtures such as those described herein. Compositions including (1R,4R,7R)-7-bromo-2-(4-methoxybenzyl)-2-azabicyclo[2.2.1]heptane-3,6-dione (5) or a salt thereof may include polar solvents, e.g., aqueous, methanol, ethanol, DMF, acetic acid, etc. or non-polar solvents, e.g., diethyl ether, hexane, dichloromethane, ethyl acetate, etc. Compositions including (1R,4R,7R)-7-bromo-2-(4-methoxybenzyl)-2-azabicyclo[2.2.1]heptane-3,6-dione (5) or a pharmaceutically acceptable salt thereof can be pharmaceutical compositions. Compositions can include (1R,4R,7R)-7-bromo-2-(4-methoxybenzyl)-2-azabicyclo[2.2.1]heptane-3,6-dione (5) or a salt thereof in amounts of from 0.0001 mg to 50 mg or more. For example, a pharmaceutical composition may include (1R,4R,7R)-7-bromo-2-(4-methoxybenzyl)-2-azabicyclo[2.2.1]heptane-3,6-dione (5) or a pharmaceutically acceptable salt thereof in amounts greater than 0.0001 mg, e.g., from 0.0001 mg to 0.0002 mg, 0.0001 mg to 0.0003 mg, 0.0002 mg to 0.0003 mg, 0.0003 mg to 0.0004 mg, 0.0004 mg to 0.0005 mg, 0.0005 mg to 0.0006 mg, 0.0006 mg to 0.0007 mg, 0.0007 mg to 0.0008 mg, 0.0008 mg to 0.0009 mg, 0.0009 mg to 0.001 mg, 0.001 mg to 0.002 mg, 0.002 mg to 0.003 mg, 0.003 mg to 0.004 mg, 0.004 mg to 0.005 mg, 0.005 mg to 0.006 mg, 0.006 mg to 0.007 mg, 0.007 mg to 0.008 mg, 0.008 mg to 0.009 mg, 0.009 mg to 0.01 mg, 0.01 mg to 0.02 mg, 0.02 mg to 0.03 mg, 0.03 mg to 0.04 mg, 0.04 mg to 0.05 mg, 0.05 mg to 0.06 mg, 0.06 mg to 0.07 mg, 0.07 mg to 0.08 mg, 0.08 mg to 0.09 mg, 0.09 mg to 0.1 mg, 0.1 mg to 0.2 mg, 0.2 mg to 0.3 mg, 0.3 mg to 0.4 mg, 0.4 mg to 0.5 mg, 0.5 mg to 0.6 mg, 0.6 mg to 0.7 mg, 0.7 mg to 0.8 mg, 0.8 mg to 0.9 mg, 0.9 mg to 1.0 mg, 1.0 mg to 2.0 mg, 2.0 mg to 3.0 mg, 3.0 mg to 4.0 mg, 4.0 mg to 5.0 mg, 5.0 mg to 6.0 mg, 6.0 mg to 7.0 mg, 7.0 mg to 8.0 mg, 8.0 mg to 9.0 mg, or 9.0 mg to 10 mg.

In embodiments, compositions including (1R,4R,7R)-7-bromo-6-(difluoromethylene)-2-(4-methoxybenzyl)-2-azabicyclo[2.2.1]heptan-3-one (6) or a salt thereof are provided herein.

Such compositions may include reaction mixtures such as those described herein. Compositions including (1R,4R,7R)-7-bromo-6-(difluoromethylene)-2-(4-methoxybenzyl)-2-azabicyclo[2.2.1]heptan-3-one (6) or a salt thereof may include polar solvents, e.g., aqueous, methanol, ethanol, DMF, acetic acid, etc. or non-polar solvents, e.g., diethyl ether, hexane, dichloromethane, ethyl acetate, etc. Compositions including (1R,4R,7R)-7-bromo-6-(difluoromethylene)-2-(4-methoxybenzyl)-2-azabicyclo[2.2.1]heptan-3-one (6) or a pharmaceutically acceptable salt thereof can be pharmaceutical compositions. Compositions can include (1R,4R,7R)-7-bromo-6-(difluoromethylene)-2-(4-methoxybenzyl)-2-azabicyclo[2.2.1]heptan-3-one (6) or a salt thereof in amounts of from 0.0001 mg to 50 mg or more. For example, a pharmaceutical composition may include (1R,4R,7R)-7-bromo-6-(difluoromethylene)-2-(4-methoxybenzyl)-2-azabicyclo[2.2.1]heptan-3-one (6) or a pharmaceutically acceptable salt thereof in amounts greater than 0.0001 mg, e.g., from 0.0001 mg to 0.0002 mg, 0.0001 mg to 0.0003 mg, 0.0002 mg to 0.0003 mg, 0.0003 mg to 0.0004 mg, 0.0004 mg to 0.0005 mg, 0.0005 mg to 0.0006 mg, 0.0006 mg to 0.0007 mg, 0.0007 mg to 0.0008 mg, 0.0008 mg to 0.0009 mg, 0.0009 mg to 0.001 mg, 0.001 mg to 0.002 mg, 0.002 mg to 0.003 mg, 0.003 mg to 0.004 mg, 0.004 mg to 0.005 mg, 0.005 mg to 0.006 mg, 0.006 mg to 0.007 mg, 0.007 mg to 0.008 mg, 0.008 mg to 0.009 mg, 0.009 mg to 0.01 mg, 0.01 mg to 0.02 mg, 0.02 mg to 0.03 mg, 0.03 mg to 0.04 mg, 0.04 mg to 0.05 mg, 0.05 mg to 0.06 mg, 0.06 mg to 0.07 mg, 0.07 mg to 0.08 mg, 0.08 mg to 0.09 mg, 0.09 mg to 0.1 mg, 0.1 mg to 0.2 mg, 0.2 mg to 0.3 mg, 0.3 mg to 0.4 mg, 0.4 mg to 0.5 mg, 0.5 mg to 0.6 mg, 0.6 mg to 0.7 mg, 0.7 mg to 0.8 mg, 0.8 mg to 0.9 mg, 0.9 mg to 1.0 mg, 1.0 mg to 2.0 mg, 2.0 mg to 3.0 mg, 3.0 mg to 4.0 mg, 4.0 mg to 5.0 mg, 5.0 mg to 6.0 mg, 6.0 mg to 7.0 mg, 7.0 mg to 8.0 mg, 8.0 mg to 9.0 mg, or 9.0 mg to 10 mg.

In embodiments, compositions (1R,4R,7R)-7-bromo-6-(difluoromethylene)-2-azabicyclo[2.2.1]heptan-3-one (7) or a salt thereof are provided herein. Such compositions may include reaction mixtures such as those described herein. Compositions including (1R,4R,7R)-7-bromo-6-(difluoromethylene)-2-azabicyclo[2.2.1]heptan-3-one (7) or a salt thereof may include polar solvents, e.g., aqueous, methanol, ethanol, DMF, acetic acid, etc. or non-polar solvents, e.g., diethyl ether, hexane, dichloromethane, ethyl acetate, etc. Compositions including (1R,4R,7R)-7-bromo-6-(difluoromethylene)-2-azabicyclo[2.2.1]heptan-3-one (7) or a pharmaceutically acceptable salt thereof can be pharmaceutical compositions. Compositions can include (1R,4R,7R)-7-bromo-6-(difluoromethylene)-2-azabicyclo[2.2.1]heptan-3-one (7) or a salt thereof in amounts of from 0.0001 mg to 50 mg or more. For example, a pharmaceutical composition may include (1R,4R,7R)-7-bromo-6-(difluoromethylene)-2-azabicyclo[2.2.1]heptan-3-one (7) or a pharmaceutically acceptable salt thereof in amounts greater than 0.0001 mg, e.g., from 0.0001 mg to 0.0002 mg, 0.0001 mg to 0.0003 mg, 0.0002 mg to 0.0003 mg, 0.0003 mg to 0.0004 mg, 0.0004 mg to 0.0005 mg, 0.0005 mg to 0.0006 mg, 0.0006 mg to 0.0007 mg, 0.0007 mg to 0.0008 mg, 0.0008 mg to 0.0009 mg, 0.0009 mg to 0.001 mg, 0.001 mg to 0.002 mg, 0.002 mg to 0.003 mg, 0.003 mg to 0.004 mg, 0.004 mg to 0.005 mg, 0.005 mg to 0.006 mg, 0.006 mg to 0.007 mg, 0.007 mg to 0.008 mg, 0.008 mg to 0.009 mg, 0.009 mg to 0.01 mg, 0.01 mg to 0.02 mg, 0.02 mg to 0.03 mg, 0.03 mg to 0.04 mg, 0.04 mg to 0.05 mg, 0.05 mg to 0.06 mg, 0.06 mg to 0.07 mg, 0.07 mg to 0.08 mg, 0.08 mg to 0.09 mg, 0.09 mg to 0.1 mg, 0.1 mg to 0.2 mg, 0.2 mg to 0.3 mg, 0.3 mg to 0.4 mg, 0.4 mg to 0.5 mg, 0.5 mg to 0.6 mg, 0.6 mg to 0.7 mg, 0.7 mg to 0.8 mg, 0.8 mg to 0.9 mg, 0.9 mg to 1.0 mg, 1.0 mg to 2.0 mg, 2.0 mg to 3.0 mg, 3.0 mg to 4.0 mg, 4.0 mg to 5.0 mg, 5.0 mg to 6.0 mg, 6.0 mg to 7.0 mg, 7.0 mg to 8.0 mg, 8.0 mg to 9.0 mg, or 9.0 mg to 10 mg.

In embodiments, compositions including (1R,4R,7R)-7-bromo-6-(difluoromethylene)-2-(tert-butoxycarbonyl)-2-azabicyclo[2.2.1]heptan-3-one (8) or a salt thereof are provided herein. Such compositions may include reaction mixtures such as those described herein. Compositions including (1R,4R,7R)-7-bromo-6-(difluoromethylene)-2-(tert-butoxycarbonyl)-2-azabicyclo[2.2.1]heptan-3-one (8) or a salt thereof may include polar solvents, e.g., aqueous, methanol, ethanol, DMF, acetic acid, etc. or non-polar solvents, e.g., diethyl ether, hexane, dichloromethane, ethyl acetate, etc. Compositions including (1R,4R,7R)-7-bromo-6-(difluoromethylene)-2-(tert-butoxycarbonyl)-2-azabicyclo[2.2.1]heptan-3-one (8) or a pharmaceutically acceptable salt thereof can be pharmaceutical compositions. Compositions can include (1R,4R,7R)-7-bromo-6-(difluoromethylene)-2-(tert-butoxycarbonyl)-2-azabicyclo[2.2.1]heptan-3-one (8) or a salt thereof in amounts of from 0.0001 mg to 50 mg or more. For example, a pharmaceutical composition can include (1R,4R,7R)-7-bromo-6-(difluoromethylene)-2-(tert-butoxycarbonyl)-2-azabicyclo[2.2.1]heptan-3-one (8) or a pharmaceutically acceptable salt thereof in amounts greater than 0.0001 mg, e.g., from 0.0001 mg to 0.0002 mg, 0.0001 mg to 0.0003 mg, 0.0002 mg to 0.0003 mg, 0.0003 mg to 0.0004 mg, 0.0004 mg to 0.0005 mg, 0.0005 mg to 0.0006 mg, 0.0006 mg to 0.0007 mg, 0.0007 mg to 0.0008 mg, 0.0008 mg to 0.0009 mg, 0.0009 mg to 0.001 mg, 0.001 mg to 0.002 mg, 0.002 mg to 0.003 mg, 0.003 mg to 0.004 mg, 0.004 mg to 0.005 mg, 0.005 mg to 0.006 mg, 0.006 mg to 0.007 mg, 0.007 mg to 0.008 mg, 0.008 mg to 0.009 mg, 0.009 mg to 0.01 mg, 0.01 mg to 0.02 mg, 0.02 mg to 0.03 mg, 0.03 mg to 0.04 mg, 0.04 mg to 0.05 mg, 0.05 mg to 0.06 mg, 0.06 mg to 0.07 mg, 0.07 mg to 0.08 mg, 0.08 mg to 0.09 mg, 0.09 mg to 0.1 mg, 0.1 mg to 0.2 mg, 0.2 mg to 0.3 mg, 0.3 mg to 0.4 mg, 0.4 mg to 0.5 mg, 0.5 mg to 0.6 mg, 0.6 mg to 0.7 mg, 0.7 mg to 0.8 mg, 0.8 mg to 0.9 mg, 0.9 mg to 1.0 mg, 1.0 mg to 2.0 mg, 2.0 mg to 3.0 mg, 3.0 mg to 4.0 mg, 4.0 mg to 5.0 mg, 5.0 mg to 6.0 mg, 6.0 mg to 7.0 mg, 7.0 mg to 8.0 mg, 8.0 mg to 9.0 mg, or 9.0 mg to 10 mg.

In embodiments, compositions including (S)-3-((tert-butoxycarbonyl)amino)-4-(difluoromethylene)cyclopent-1-ene-1-carboxylate (9) or a salt thereof are provided herein. Such compositions may include reaction mixtures such as those described herein. Compositions including (S)-3-((tert-butoxycarbonyl)amino)-4-(difluoromethylene)cyclopent-1-ene-1-carboxylate (9) or a salt thereof may include polar solvents, e.g., aqueous, methanol, ethanol, DMF, acetic acid, etc. or non-polar solvents, e.g., diethyl ether, hexane, dichloromethane, ethyl acetate, etc. Compositions including (S)-3-((tert-butoxycarbonyl)amino)-4-(difluoromethylene)cyclopent-1-ene-1-carboxylate (9) or a pharmaceutically acceptable salt thereof can be pharmaceutical compositions. Compositions can include (S)-3-((tert-butoxycarbonyl)

amino)-4-(difluoromethylene)cyclopent-1-ene-1-carboxylate (9) or a salt thereof in amounts of from 0.0001 mg to 50 mg or more. For example, a pharmaceutical composition may include (S)-3-((tert-butoxycarbonyl)amino)-4-(difluoromethylene)cyclopent-1-ene-1-carboxylate (9) or a pharmaceutically acceptable salt thereof in amounts greater than 0.0001 mg, e.g., from 0.0001 mg to 0.0002 mg, 0.0001 mg to 0.0003 mg, 0.0002 mg to 0.0003 mg, 0.0003 mg to 0.0004 mg, 0.0004 mg to 0.0005 mg, 0.0005 mg to 0.0006 mg, 0.0006 mg to 0.0007 mg, 0.0007 mg to 0.0008 mg, 0.0008 mg to 0.0009 mg, 0.0009 mg to 0.001 mg, 0.001 mg to 0.002 mg, 0.002 mg to 0.003 mg, 0.003 mg to 0.004 mg, 0.004 mg to 0.005 mg, 0.005 mg to 0.006 mg, 0.006 mg to 0.007 mg, 0.007 mg to 0.008 mg, 0.008 mg to 0.009 mg, 0.009 mg to 0.01 mg, 0.01 mg to 0.02 mg, 0.02 mg to 0.03 mg, 0.03 mg to 0.04 mg, 0.04 mg to 0.05 mg, 0.05 mg to 0.06 mg, 0.06 mg to 0.07 mg, 0.07 mg to 0.08 mg, 0.08 mg to 0.09 mg, 0.09 mg to 0.1 mg, 0.1 mg to 0.2 mg, 0.2 mg to 0.3 mg, 0.3 mg to 0.4 mg, 0.4 mg to 0.5 mg, 0.5 mg to 0.6 mg, 0.6 mg to 0.7 mg, 0.7 mg to 0.8 mg, 0.8 mg to 0.9 mg, 0.9 mg to 1.0 mg, 1.0 mg to 2.0 mg, 2.0 mg to 3.0 mg, 3.0 mg to 4.0 mg, 4.0 mg to 5.0 mg, 5.0 mg to 6.0 mg, 6.0 mg to 7.0 mg, 7.0 mg to 8.0 mg, 8.0 mg to 9.0 mg, or 9.0 mg to 10 mg.

In embodiments, synthesis of (S)-3-amino-4-(difluoromethylenyl)cyclopent-1-ene-1-carboxylic acid (1) is shown in Scheme 2 starting with ethyl-cyclopent-3-ene-carboxylate (10).

As depicted in Scheme 2, a process for preparing (S)-3-amino-4-(difluoromethylenyl)cyclopent-1-ene-1-carboxylic acid (1) is provided which includes converting ethyl-cyclopent-3-ene-carboxylate (10) to (3R,4S)-ethyl-3-((tert-butoxycarbonyl)amino)-4-(hydroxy)cyclopentane carboxylate (11). (3R,4S)-Ethyl-3-((tert-butoxycarbonyl)amino)-4-(hydroxy)cyclopentane carboxylate (11) is converted to (3R)-ethyl-3-((tert-butoxycarbonyl)amino)-4-oxo-cyclopentane carboxylate (12). (3R)-Ethyl-3-((tert-butoxycarbonyl)amino)-4-oxo-cyclopentane carboxylate is converted to ethyl (9S)-9-(tert-butoxycarbonylamino)-1,4-dioxa-7-spiro[4.4]nonanecarboxylate (13). Ethyl (9S)-9-(tert-butoxycarbonylamino)-1,4-dioxa-7-spiro[4.4]nonanecarboxylate (13) is converted to ethyl (S)-9-(tert-butoxycarbonylamino)-1,4-dioxa-7-spiro[4.4]nonene-7-carboxylate (14). Ethyl (S)-9-(tert-butoxycarbonylamino)-1,4-dioxa-7-spiro[4.4]nonene-7-carboxylate (14) is converted to ethyl (S)-3-((tert-butoxycarbonyl)amino)-4-(difluoromethylene)cyclopent-1-ene-1-carboxylate (15).

Ethyl (S)-3-((tert-butoxycarbonyl)amino)-4-(difluoromethylene)cyclopent-1-ene-1-carboxylate (15) is converted to (S)-3-amino-4-(difluoromethylenyl)cyclopent-1-ene-1-carboxylic acid (1).

In embodiments, synthesis of (S)-3-amino-4-(difluoromethylenyl)cyclopent-1-ene-1-carboxylic acid (1) is shown in Scheme 2A.

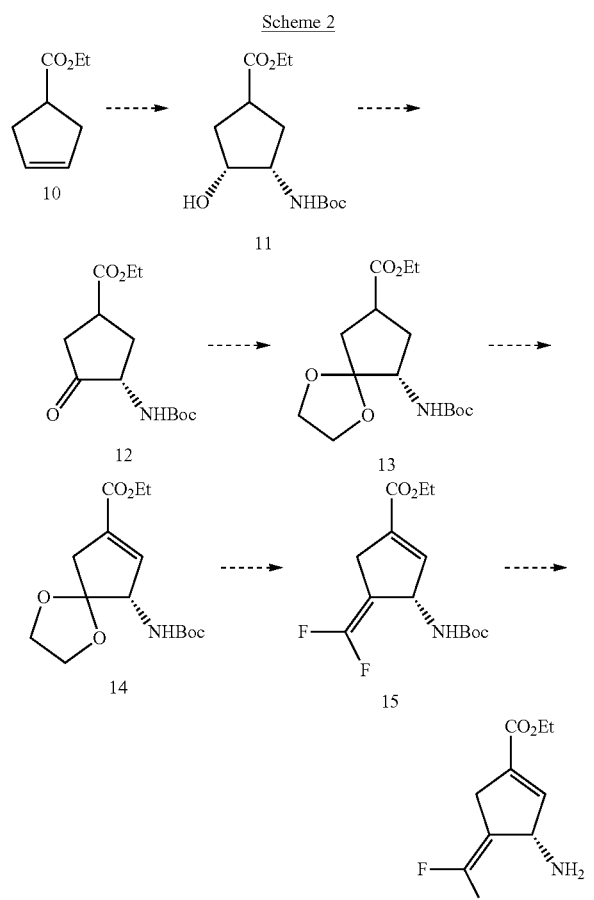

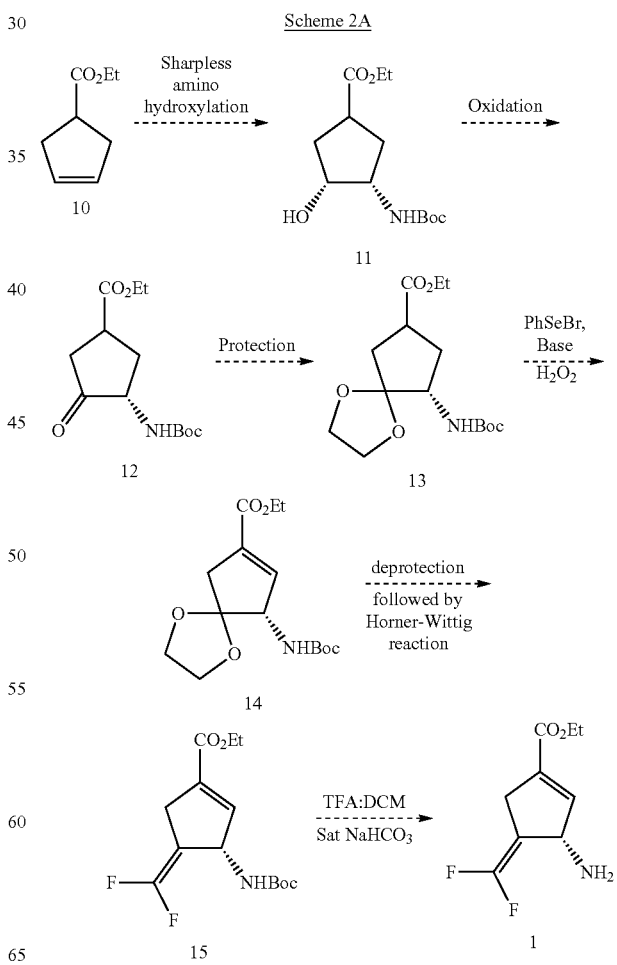

In embodiments, as shown in Scheme 2A, ethyl-cyclopent-3-ene-carboxylate (10) (commercially available from Sigma Aldrich, St. Louis, MO) is converted to (3R,4S)-ethyl-3-((tert-butoxycarbonyl)amino)-4-(hydroxy)cyclopentane carboxylate (11) by Sharpless aminohydroxylation and Boc protection. Sharpless aminohydroxylation allows the syn-selective preparation of 1,2-amino alcohols by reaction of alkenes with salts of N-halosulfonamides,-amides and carbamates using $OsO_4$ as a catalyst. Enantioselectivity is achieved through the addition of dihydroquinine- and dihydroquinidine-derived chiral ligands. Oxidation of (3R,4S)-ethyl-3-((tert-butoxycarbonyl)amino)-4-(hydroxy)cyclopentane carboxylate (11) yields ketone (3R)-ethyl-3-((tert-butoxycarbonyl)amino)-4-oxo-cyclopentane carboxylate (12). (3R)-ethyl-3-((tert-butoxycarbonyl)amino)-4-oxo-cyclopentane carboxylate (12) is converted to ethyl (9S)-9-(tert-butoxycarbonylamino)-1,4-dioxa-7-spiro[4.4]nonanecarboxylate (13). Ethyl (9S)-9-(tert-butoxycarbonylamino)-1,4-dioxa-7-spiro[4.4]nonanecarboxylate (13) is subjected to phenyl selenium bromide, Base and $H_2O_2$ to yield Ethyl (S)-9-(tert-butoxycarbonylamino)-1,4-dioxa-7-spiro[4.4]nonene-7-carboxylate (14). Ethyl (S)-9-(tert-butoxycarbonylamino)-1,4-dioxa-7-spiro[4.4]nonene-7-carboxylate (14) is deprotected and subjected to Horner-Wittig reaction to yield ethyl (S)-3-((tert-butoxycarbonyl)amino)-4-(difluoromethylene)cyclopent-1-ene-1-carboxylate (15). The Horner-Wittig reaction involves the reaction of aldehydes or ketones with stabilized phosphorus ylides (phosphonate carbanions) and leads to olefins with E-selectivity.

Ethyl (S)-3-((tert-butoxycarbonyl)amino)-4-(difluoromethylene)cyclopent-1-ene-1-carboxylate (15) is converted to (S)-3-amino-4-(difluoromethylenyl)cyclopent-1-ene-1-carboxylic acid (1) with trifluoroacetic acid (TFA), dichloromethane (DCM) and saturated $NaHCO_3$.

In embodiments, the following compounds are provided:

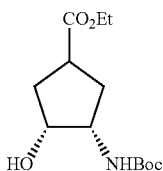

(3R,4S)-ethyl-3-((tert-butoxycarbonyl)amino)-4-(hydroxy) cyclopentane carboxylate (11)

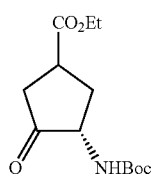 [SMILES: CCOC(=O)C1CC(=O)[C@@H](NC(=O)OC(C)(C)C)C1]

(3R)-ethyl-3-((tert-butoxycarbonyl)amino)-4-oxo-cyclopentane carboxylate (12)

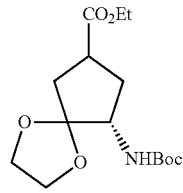

Ethyl (9S)-9-(tert-butoxycarbonylamino)-1,4-dioxa-7-spiro[4.4]nonanecarboxylate (13)

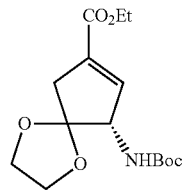

Ethyl (S)-9-(tert-butoxycarbonylamino)-1,4-dioxa-7-spiro[4.4]nonene-7-carboxylate (14)

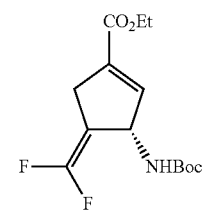 [SMILES: CCOC(=O)C1=C[C@H](NC(=O)OC(C)(C)C)C(=C(F)F)C1]

Ethyl (S)-3-((tert-butoxycarbonyl)amino)-4-(difluoromethylene)cyclopent-1-ene-1-carboxylate (15)

In embodiments, compositions including (3R,4S)-ethyl-3-((tert-butoxycarbonyl)amino)-4-(hydroxy)cyclopentane carboxylate (11) or a salt thereof are provided herein. Such compositions may include reaction mixtures such as those described herein. Compositions (3R,4S)-ethyl-3-((tert-butoxycarbonyl)amino)-4-(hydroxy)cyclopentane carboxylate (11) or a salt thereof may include polar solvents, e.g., aqueous, methanol, ethanol, DMF, acetic acid, etc. or nonpolar solvents, e.g., diethyl ether, hexane, dichloromethane, ethyl acetate, etc. Compositions including (3R,4S)-ethyl-3-((tert-butoxycarbonyl)amino)-4-(hydroxy)cyclopentane carboxylate (11) or a pharmaceutically acceptable salt thereof can be pharmaceutical compositions.

Compositions can include (3R,4S)-ethyl-3-((tert-butoxycarbonyl)amino)-4-(hydroxy)cyclopentane carboxylate (11) or a salt thereof in amounts of from 0.0001 mg to 50 mg or more. For example, a pharmaceutical composition may include (3R,4S)-ethyl-3-((tert-butoxycarbonyl)amino)-4-(hydroxy)cyclopentane carboxylate (11) or a pharmaceutically acceptable salt thereof in amounts greater than 0.0001 mg, e.g., from 0.0001 mg to 0.0002 mg, 0.0001 mg to 0.0003 mg, 0.0002 mg to 0.0003 mg, 0.0003 mg to 0.0004 mg, 0.0004 mg to 0.0005 mg, 0.0005 mg to 0.0006 mg, 0.0006 mg to 0.0007 mg, 0.0007 mg to 0.0008 mg, 0.0008 mg to 0.0009 mg, 0.0009 mg to 0.001 mg, 0.001 mg to 0.002 mg, 0.002 mg to 0.003 mg, 0.003 mg to 0.004 mg, 0.004 mg to 0.005 mg, 0.005 mg to 0.006 mg, 0.006 mg to 0.007 mg, 0.007 mg to 0.008 mg, 0.008 mg to 0.009 mg, 0.009 mg to 0.01 mg, 0.01 mg to 0.02 mg, 0.02 mg to 0.03 mg, 0.03 mg to 0.04 mg, 0.04 mg to 0.05 mg, 0.05 mg to 0.06 mg, 0.06 mg to 0.07 mg, 0.07 mg to 0.08 mg, 0.08 mg to 0.09 mg, 0.09 mg to 0.1 mg, 0.1 mg to 0.2 mg, 0.2 mg to 0.3 mg, 0.3 mg to 0.4 mg, 0.4 mg to 0.5 mg, 0.5 mg to 0.6 mg, 0.6 mg to 0.7 mg, 0.7 mg to 0.8 mg, 0.8 mg to 0.9 mg, 0.9 mg to 1.0 mg, 1.0 mg to 2.0 mg, 2.0 mg to 3.0 mg, 3.0 mg to 4.0 mg, 4.0 mg to 5.0 mg, 5.0 mg to 6.0 mg, 6.0 mg to 7.0 mg, 7.0 mg to 8.0 mg, 8.0 mg to 9.0 mg, or 9.0 mg to 10 mg.

In embodiments, compositions including (3R)-ethyl-3-((tert-butoxycarbonyl)amino)-4-oxo-cyclopentane carboxylate (12) or a salt thereof are provided herein. Such compositions may include reaction mixtures such as those described herein. Compositions including (3R)-ethyl-3-((tert-butoxycarbonyl)amino)-4-oxo-cyclopentane carboxylate (12) or a salt thereof may include polar solvents, e.g., aqueous, methanol, ethanol, DMF, acetic acid, etc. or non-polar solvents, e.g., diethyl ether, hexane, dichloromethane, ethyl acetate, etc. Compositions including (3R)-ethyl-3-((tert-butoxycarbonyl)amino)-4-oxo-cyclopentane carboxylate (12) or a pharmaceutically acceptable salt thereof can be pharmaceutical compositions. Compositions can include (3R)-ethyl-3-((tert-butoxycarbonyl)amino)-4-oxo-cyclopentane carboxylate (12) or a salt thereof in amounts of from 0.0001 mg to 50 mg or more. For example, a pharmaceutical composition can include ((3R)-ethyl-3-((tert-butoxycarbonyl)amino)-4-oxo-cyclopentane carboxylate (12) or a pharmaceutically acceptable salt thereof in amounts greater than 0.0001 mg, e.g., from 0.0001 mg to 0.0002 mg, 0.0001 mg to 0.0003 mg, 0.0002 mg to 0.0003 mg, 0.0003 mg to 0.0004 mg, 0.0004 mg to 0.0005 mg, 0.0005 mg to 0.0006 mg, 0.0006 mg to 0.0007 mg, 0.0007 mg to 0.0008 mg, 0.0008 mg to 0.0009 mg, 0.0009 mg to 0.001 mg, 0.001 mg to 0.002 mg, 0.002 mg to 0.003 mg, 0.003 mg to 0.004 mg, 0.004 mg to 0.005 mg, 0.005 mg to 0.006 mg, 0.006 mg to 0.007 mg, 0.007 mg to 0.008 mg, 0.008 mg to 0.009 mg, 0.009 mg to 0.01 mg, 0.01 mg to 0.02 mg, 0.02 mg to 0.03 mg, 0.03 mg to 0.04 mg, 0.04 mg to 0.05 mg, 0.05 mg to 0.06 mg, 0.06 mg to 0.07 mg, 0.07 mg to 0.08 mg, 0.08 mg to 0.09 mg, 0.09 mg to 0.1 mg, 0.1 mg to 0.2 mg, 0.2 mg to 0.3 mg, 0.3 mg to 0.4 mg, 0.4 mg to 0.5 mg, 0.5 mg to 0.6 mg, 0.6 mg to 0.7 mg, 0.7 mg to 0.8 mg, 0.8 mg to 0.9 mg, 0.9 mg to 1.0 mg, 1.0 mg to 2.0 mg, 2.0 mg to 3.0 mg, 3.0 mg to 4.0 mg, 4.0 mg to 5.0 mg, 5.0 mg to 6.0 mg, 6.0 mg to 7.0 mg, 7.0 mg to 8.0 mg, 8.0 mg to 9.0 mg, or 9.0 mg to 10 mg.

In embodiments, compositions including ethyl (9S)-9-(tert-butoxycarbonylamino)-1,4-dioxa-7-spiro[4.4]nonanecarboxylate (13) or a salt thereof are provided herein. Such compositions may include reaction mixtures such as those described herein. Compositions including including ethyl (9S)-9-(tert-butoxycarbonylamino)-1,4-dioxa-7-spiro[4.4] nonanecarboxylate (13) or a salt thereof may include polar solvents, e.g., aqueous, methanol, ethanol, DMF, acetic acid, etc. or non-polar solvents, e.g., diethyl ether, hexane, dichloromethane, ethyl acetate, etc. Compositions including including ethyl (9S)-9-(tert-butoxycarbonylamino)-1,4-dioxa-7-spiro[4.4]nonanecarboxylate (13) or a pharmaceutically acceptable salt thereof can be pharmaceutical compositions. Compositions can include including ethyl (9S)-9-(tert-butoxycarbonylamino)-1,4-dioxa-7-spiro[4.4] nonanecarboxylate (13) or a salt thereof in amounts of from 0.0001 mg to 50 mg or more. For example, a pharmaceutical composition can include including ethyl (9S)-9-(tert-butoxycarbonylamino)-1,4-dioxa-7-spiro[4.4]nonanecarboxylate (13) or a pharmaceutically acceptable salt thereof in amounts greater than 0.0001 mg, e.g., from 0.0001 mg to 0.0002 mg, 0.0001 mg to 0.0003 mg, 0.0002 mg to 0.0003 mg, 0.0003 mg to 0.0004 mg, 0.0004 mg to 0.0005 mg, 0.0005 mg to 0.0006 mg, 0.0006 mg to 0.0007 mg, 0.0007 mg to 0.0008 mg, 0.0008 mg to 0.0009 mg, 0.0009 mg to 0.001 mg, 0.001 mg to 0.002 mg, 0.002 mg to 0.003 mg, 0.003 mg to 0.004 mg, 0.004 mg to 0.005 mg, 0.005 mg to 0.006 mg, 0.006 mg to 0.007 mg, 0.007 mg to 0.008 mg, 0.008 mg to 0.009 mg, 0.009 mg to 0.01 mg, 0.01 mg to 0.02 mg, 0.02 mg to 0.03 mg, 0.03 mg to 0.04 mg, 0.04 mg to 0.05 mg, 0.05 mg to 0.06 mg, 0.06 mg to 0.07 mg, 0.07 mg to 0.08 mg, 0.08 mg to 0.09 mg, 0.09 mg to 0.1 mg, 0.1 mg to 0.2 mg, 0.2 mg to 0.3 mg, 0.3 mg to 0.4 mg, 0.4 mg to 0.5 mg, 0.5 mg to 0.6 mg, 0.6 mg to 0.7 mg, 0.7 mg to 0.8 mg, 0.8 mg to 0.9 mg, 0.9 mg to 1.0 mg, 1.0 mg to 2.0 mg, 2.0 mg to 3.0 mg, 3.0 mg to 4.0 mg, 4.0 mg to 5.0 mg, 5.0 mg to 6.0 mg, 6.0 mg to 7.0 mg, 7.0 mg to 8.0 mg, 8.0 mg to 9.0 mg, or 9.0 mg to 10 mg.

In embodiments, compositions including ethyl (S)-9-(tert-butoxycarbonylamino)-1,4-dioxa-7-spiro[4.4]nonene-7-carboxylate (14) or a salt thereof are provided herein. Such compositions may include reaction mixtures such as those described herein. Compositions including ethyl (S)-9-(tert-butoxycarbonylamino)-1,4-dioxa-7-spiro[4.4]nonene-7-carboxylate (14) or a salt thereof may include polar solvents, e.g., aqueous, methanol, ethanol, DMF, acetic acid, etc. or non-polar solvents, e.g., diethyl ether, hexane, dichloromethane, ethyl acetate, etc. Compositions including ethyl (S)-9-(tert-butoxycarbonylamino)-1,4-dioxa-7-spiro[4.4] nonene-7-carboxylate (14) or a pharmaceutically acceptable salt thereof can be pharmaceutical compositions. Compositions can include ethyl (S)-9-(tert-butoxycarbonylamino)-1, 4-dioxa-7-spiro[4.4]nonene-7-carboxylate (14) or a salt thereof in amounts of from 0.0001 mg to 50 mg or more. For example, a pharmaceutical composition can include ethyl (S)-9-(tert-butoxycarbonylamino)-1,4-dioxa-7-spiro[4.4] nonene-7-carboxylate (14) or a pharmaceutically acceptable salt thereof in amounts greater than 0.0001 mg, e.g., from 0.0001 mg to 0.0002 mg, 0.0001 mg to 0.0003 mg, 0.0002 mg to 0.0003 mg, 0.0003 mg to 0.0004 mg, 0.0004 mg to 0.0005 mg, 0.0005 mg to 0.0006 mg, 0.0006 mg to 0.0007 mg, 0.0007 mg to 0.0008 mg, 0.0008 mg to 0.0009 mg, 0.0009 mg to 0.001 mg, 0.001 mg to 0.002 mg, 0.002 mg to 0.003 mg, 0.003 mg to 0.004 mg, 0.004 mg to 0.005 mg, 0.005 mg to 0.006 mg, 0.006 mg to 0.007 mg, 0.007 mg to 0.008 mg, 0.008 mg to 0.009 mg, 0.009 mg to 0.01 mg, 0.01 mg to 0.02 mg, 0.02 mg to 0.03 mg, 0.03 mg to 0.04 mg, 0.04 mg to 0.05 mg, 0.05 mg to 0.06 mg, 0.06 mg to 0.07 mg, 0.07 mg to 0.08 mg, 0.08 mg to 0.09 mg, 0.09 mg to 0.1 mg, 0.1 mg to 0.2 mg, 0.2 mg to 0.3 mg, 0.3 mg to 0.4 mg, 0.4 mg to 0.5 mg, 0.5 mg to 0.6 mg, 0.6 mg to 0.7 mg, 0.7 mg to 0.8 mg, 0.8 mg to 0.9 mg, 0.9 mg to 1.0 mg, 1.0 mg to 2.0 mg, 2.0 mg to 3.0 mg, 3.0 mg to 4.0 mg, 4.0 mg to 5.0 mg, 5.0 mg to 6.0 mg, 6.0 mg to 7.0 mg, 7.0 mg to 8.0 mg, 8.0 mg to 9.0 mg, or 9.0 mg to 10 mg.

In embodiments, compositions including ethyl (S)-3-((tert-butoxycarbonyl)amino)-4-(difluoromethylene)cyclopent-1-ene-1-carboxylate (15) or a salt thereof are provided herein. Such compositions may include reaction mixtures such as those described herein. Compositions including ethyl (S)-3-((tert-butoxycarbonyl)amino)-4-(difluoromethylene)cyclopent-1-ene-1-carboxylate (15) or a salt thereof may include polar solvents, e.g., aqueous, methanol, ethanol, DMF, acetic acid, etc. or non-polar solvents, e.g., diethyl ether, hexane, dichloromethane, ethyl acetate, etc. Compositions including ethyl (S)-3-((tert-butoxycarbonyl)

amino)-4-(difluoromethylene)cyclopent-1-ene-1-carboxylate (15) or a pharmaceutically acceptable salt thereof can be pharmaceutical compositions. Compositions can include ethyl (S)-3-((tert-butoxycarbonyl)amino)-4-(difluoromethylene)cyclopent-1-ene-1-carboxylate (15) or a salt thereof in amounts of from 0.0001 mg to 50 mg or more. For example, a pharmaceutical composition can include ethyl (S)-3-((tert-butoxycarbonyl)amino)-4-(difluoromethylene)cyclopent-1-ene-1-carboxylate (15) or a pharmaceutically acceptable salt thereof in amounts greater than 0.0001 mg, e.g., from 0.0001 mg to 0.0002 mg, 0.0001 mg to 0.0003 mg, 0.0002 mg to 0.0003 mg, 0.0003 mg to 0.0004 mg, 0.0004 mg to 0.0005 mg, 0.0005 mg to 0.0006 mg, 0.0006 mg to 0.0007 mg, 0.0007 mg to 0.0008 mg, 0.0008 mg to 0.0009 mg, 0.0009 mg to 0.001 mg, 0.001 mg to 0.002 mg, 0.002 mg to 0.003 mg, 0.003 mg to 0.004 mg, 0.004 mg to 0.005 mg, 0.005 mg to 0.006 mg, 0.006 mg to 0.007 mg, 0.007 mg to 0.008 mg, 0.008 mg to 0.009 mg, 0.009 mg to 0.01 mg, 0.01 mg to 0.02 mg, 0.02 mg to 0.03 mg, 0.03 mg to 0.04 mg, 0.04 mg to 0.05 mg, 0.05 mg to 0.06 mg, 0.06 mg to 0.07 mg, 0.07 mg to 0.08 mg, 0.08 mg to 0.09 mg, 0.09 mg to 0.1 mg, 0.1 mg to 0.2 mg, 0.2 mg to 0.3 mg, 0.3 mg to 0.4 mg, 0.4 mg to 0.5 mg, 0.5 mg to 0.6 mg, 0.6 mg to 0.7 mg, 0.7 mg to 0.8 mg, 0.8 mg to 0.9 mg, 0.9 mg to 1.0 mg, 1.0 mg to 2.0 mg, 2.0 mg to 3.0 mg, 3.0 mg to 4.0 mg, 4.0 mg to 5.0 mg, 5.0 mg to 6.0 mg, 6.0 mg to 7.0 mg, 7.0 mg to 8.0 mg, 8.0 mg to 9.0 mg, or 9.0 mg to 10 mg.

In embodiments, pharmaceutical compositions may include (S)-3-amino-4-(difluoromethylenyl)cyclopent-1-ene-1-carboxylic acid or a pharmaceutically acceptable salt thereof in an amount of, e.g., about 0.001 to 500 mg, 0.01 to 500 mg, 0.01 to 450 mg, 0.01 to 300 mg, 0.01 to 250 mg, 0.01 to 200 mg, 0.01 to 175 mg, 0.01 to 150 mg, 0.01 to 125 mg, 0.01 to 100 mg, 0.01 to 75 mg, 0.01 to 50 mg, 0.01 to 30 mg, 0.01 to 25 mg, 0.01 to 20 mg, 0.01 to 15 mg, 0.01 to 10 mg, 0.01 to 5 mg, 0.01 to 1 mg, 0.025 to 500 mg, 0.025 to 450 mg, 0.025 to 300 mg, 0.025 to 250 mg, 0.025 to 200 mg, 0.025 to 175 mg, 0.025 to 150 mg, 0.025 to 125 mg, 0.025 to 100 mg, 0.025 to 75 mg, 0.025 to 50 mg, 0.025 to 30 mg, 0.025 to 25 mg, 0.025 to 20 mg, 0.025 to 15 mg, 0.025 to 10 mg, 0.025 to 5 mg, 0.025 to 1 mg, 0.05 to 500 mg, 0.05 to 450 mg, 0.05 to 300 mg, 0.05 to 250 mg, 0.05 to 200 mg, 0.05 to 175 mg, 0.05 to 150 mg, 0.05 to 125 mg, 0.05 to 100 mg, 0.05 to 75 mg, 0.05 to 50 mg, 0.05 to 30 mg, 0.05 to 25 mg, 0.05 to 20 mg, 0.05 to 15 mg, 0.05 to 10 mg, 0.05 to 5 mg, 0.05 to 1 mg, 0.075 to 500 mg, 0.075 to 450 mg, 0.075 to 300 mg, 0.075 to 250 mg, 0.075 to 200 mg, 0.075 to 175 mg, 0.075 to 150 mg, 0.075 to 125 mg, 0.075 to 100 mg, 0.075 to 75 mg, 0.075 to 50 mg, 0.075 to 30 mg, 0.075 to 25 mg, 0.075 to 20 mg, 0.075 to 15 mg, 0.075 to 10 mg, 0.075 to 5 mg, 0.075 to 1 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 0.25 to 500 mg, 0.25 to 450 mg, 0.25 to 300 mg, 0.25 to 250 mg, 0.25 to 200 mg, 0.25 to 175 mg, 0.25 to 150 mg, 0.25 to 125 mg, 0.25 to 100 mg, 0.25 to 75 mg, 0.25 to 50 mg, 0.25 to 30 mg, 0.25 to 25 mg, 0.25 to 20 mg, 0.25 to 15 mg, 0.25 to 10 mg, 0.25 to 5 mg, 0.25 to 1 mg, 0.05 to 500 mg, 0.5 to 450 mg, 0.5 to 300 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 1 mg, 1 to 500 mg, 1 to 450 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 1 to 4 mg, 1 to 3 mg, 1 to 2 mg, 2 to 500 mg, 2 to 450 mg, 2 to 300 mg, 2 to 250 mg, 2 to 200 mg, 2 to 175 mg, 2 to 150 mg, 2 to 125 mg, 2 to 100 mg, 2 to 75 mg, 2 to 50 mg, 2 to 30 mg, 2 to 25 mg, 2 to 20 mg, 2 to 15 mg, 2 to 10 mg, 2 to 5 mg, 3 to 500 mg, 3 to 450 mg, 3 to 300 mg, 3 to 250 mg, 3 to 200 mg, 3 to 175 mg, 3 to 150 mg, 3 to 125 mg, 3 to 100 mg, 3 to 75 mg, 3 to 50 mg, 3 to 30 mg, 3 to 25 mg, 3 to 20 mg, 3 to 15 mg, 3 to 10 mg, 3 to 5 mg, 4 to 500 mg, 4 to 450 mg, 4 to 300 mg, 4 to 250 mg, 4 to 200 mg, 4 to 175 mg, 4 to 150 mg, 4 to 125 mg, 4 to 100 mg, 4 to 75 mg, 4 to 50 mg, 4 to 30 mg, 4 to 25 mg, 4 to 20 mg, 4 to 15 mg, 4 to 10 mg, 4 to 5 mg, 5 to 500 mg, 5 to 450 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 500 mg, 10 to 450 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 500 mg, 15 to 450 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 500 mg, 20 to 450 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 500 mg, 25 to 450 mg, 25 to 300 mg, 25 to 250 mg, 25 to 200 mg, 25 to 175 mg, 25 to 150 mg, 25 to 125 mg, 25 to 100 mg, 25 to 80 mg, 25 to 75 mg, 25 to 50 mg, 25 to 30 mg, 30 to 500 mg, 30 to 450 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 40 to 500 mg, 40 to 450 mg, 40 to 400 mg, 40 to 250 mg, 40 to 200 mg, 40 to 175 mg, 40 to 150 mg, 40 to 125 mg, 40 to 100 mg, 40 to 75 mg, 40 to 50 mg, 50 to 500 mg, 50 to 450 mg, 50 to 300 mg, 50 to 250 mg, 50 to 200 mg, 50 to 175 mg, 50 to 150 mg, 50 to 125 mg, 50 to 100 mg, 50 to 75 mg, 75 to 500 mg, 75 to 450 mg, 75 to 300 mg, 75 to 250 mg, 75 to 200 mg, 75 to 175 mg, 75 to 150 mg, 75 to 125 mg, 75 to 100 mg, 100 to 500 mg, 100 to 450 mg, 100 to 300 mg, 100 to 250 mg, 100 to 200 mg, 100 to 175 mg, 100 to 150 mg, 100 to 125 mg, 125 to 500 mg, 125 to 450 mg, 125 to 300 mg, 125 to 250 mg, 125 to 200 mg, 125 to 175 mg, 125 to 150 mg, 150 to 500 mg, 150 to 450 mg, 150 to 300 mg, 150 to 250 mg, 150 to 200 mg, 200 to 500 mg, 200 to 450 mg, 200 to 300 mg, 200 to 250 mg, 250 to 500 mg, 250 to 450 mg, 250 to 300 mg, 300 to 500 mg, 300 to 450 mg, 300 to 400 mg, 300 to 350 mg, 350 to 500 mg, 350 to 450 mg, 350 to 400 mg, 400 to 500 mg, 400 to 450 mg, with 0.01 mg, 0.025 mg, 0.05 mg, 0.075 mg, 0.1 mg, 0.25 mg, 0.5 mg, 0.75 mg, 1 mg, 2 mg, 2.5 mg, 3 mg, 4 mg, 5 mg, 7.5 mg, 10 mg, 12.5 mg, 15 mg, 17.5 mg, 20 mg, 22.5 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg 175 mg, 200 mg, 225 mg, 250 mg, 275 mg, 300 mg, 325 mg, 350 mg, 375 mg, 400 mg, 425 mg, 450 mg, 475 mg, and 500 mg being examples.

In embodiments, pharmaceutical compositions including (S)-3-amino-4-(difluoromethylenyl)cyclopent-1-ene-1-carboxylic acid (1) and one or more of (1R,4S)-2-Azabicyclo[2.2.1]hept-5-en-3-one (2), (1R,4S)-2-(4-methoxybenzyl)-2-azabicyclo[2.2.1]hept-5-en-3-one (3), (1R,4R,6S,7R)-7-bromo-2-(4-methoxybenzyl)-3-oxo-2-azabicyclo[2.2.1]heptan-6-yl acetate (4), (1R,4R,6S,7R)-7-bromo-6-hydroxy-2-(4-methoxybenzyl)-2-azabicyclo[2.2.1]heptan-3-one (25), (1R,4R,7R)-7-bromo-2-(4-methoxybenzyl)-2-azabicyclo[2.2.1]heptane-3,6-dione (5), (1R,4R,7R)-7-bromo-6-(difluoromethylene)-2-azabicyclo[2.2.1]heptan-3-one (6), (1R,4R,7R)-7-bromo-6-(difluoromethylene)-2-azabicyclo[2.2.1]heptan-3-one (7), (1R,4R,7R)-7-bromo-6-(difluoromethylene)-2-(tert-butoxycarbonyl)-2-azabicyclo[2.2.1]heptan-3-one (8), (S)-3-((Tert-butoxycarbonyl)amino)-4-(difluoromethylene)cyclopent-1-ene-1-carboxylic acid (19), or methyl (S)-3-((tert-butoxycarbonyl)amino)-4-(difluoromethylene)cyclopent-1-ene-1-carboxylate (9) are provided.

In embodiments, pharmaceutical compositions including (S)-3-amino-4-(difluoromethylenyl)cyclopent-1-ene-1-carboxylic acid (1) and one or more of ethyl-cyclopent-3-ene-carboxylate (10), (3R,4S)-ethyl-3-((tert-butoxycarbonyl)amino)-4-(hydroxy)cyclopentane carboxylate (11), (3R)-ethyl-3-((tert-butoxycarbonyl)amino)-4-oxo-cyclopentane carboxylate (12), ethyl (9S)-9-(tert-butoxycarbonylamino)-1,4-dioxa-7-spiro[4.4]nonanecarboxylate (13), ethyl (S)-9-(tert-butoxycarbonylamino)-1,4-dioxa-7-spiro[4.4]nonene-7-carboxylate (14), or ethyl (S)-3-((tert-butoxycarbonyl)amino)-4-(difluoromethylene)cyclopent-1-ene-1-carboxylate (15), are provided.

In embodiments, (S)-3-amino-4-(difluoromethylenyl)cyclopent-1-ene-1-carboxylic acid may be provided as an acid addition salt, a zwitter ion hydrate, zwitter ion anhydrate, hydrochloride or hydrobromide salt, or in the form of the zwitter ion monohydrate. Acid addition salts, include but are not limited to, maleic, fumaric, benzoic, ascorbic, succinic, oxalic, bis-methylenesalicylic, methanesulfonic, ethane-disulfonic, acetic, propionic, tartaric, salicylic, citric, gluconic, lactic, malic, mandelic, cinnamic, citraconic, aspartic, stearic, palmitic, itaconic, glycolic, pantothenic, p-amino-benzoic, glutamic, benzene sulfonic or theophylline acetic acid addition salts, as well as the 8-halotheophyllines, for example 8-bromo-theophylline. In embodiments, inorganic acid addition salts, including but not limited to, hydrochloric, hydrobromic, hydroiodic, sulfuric, sulfamic, phosphoric or nitric acid addition salts may be used.

In embodiments, (1R,4S)-2-(4-methoxybenzyl)-2-azabicyclo[2.2.1]hept-5-en-3-one (3), (1R,4R,6S,7R)-7-bromo-2-(4-methoxybenzyl)-3-oxo-2-azabicyclo[2.2.1]heptan-6-yl acetate (4), (1R,4R,7R)-7-bromo-2-(4-methoxybenzyl)-2-azabicyclo[2.2.1]heptane-3,6-dione (5), (1R,4R,7R)-7-bromo-6-(difluoromethylene)-2-azabicyclo[2.2.1]heptan-3-one (6), (1R,4R,7R)-7-bromo-6-(difluoromethylene)-2-azabicyclo[2.2.1]heptan-3-one (7), (1R,4R,7R)-7-bromo-6-(difluoromethylene)-2-(tert-butoxycarbonyl)-2-azabicyclo[2.2.1]heptan-3-one (8), or methyl (S)-3-((tert-butoxycarbonyl)amino)-4-(difluoromethylene)cyclopent-1-ene-1-carboxylate (9) may be provided as an acid addition salt, a zwitter ion hydrate, zwitter ion anhydrate, hydrochloride or hydrobromide salt, or in the form of the zwitter ion monohydrate. Acid addition salts, include but are not limited to, maleic, fumaric, benzoic, ascorbic, succinic, oxalic, bis-methylenesalicylic, methanesulfonic, ethane-disulfonic, acetic, propionic, tartaric, salicylic, citric, gluconic, lactic, malic, mandelic, cinnamic, citraconic, aspartic, stearic, palmitic, itaconic, glycolic, pantothenic, p-amino-benzoic, glutamic, benzene sulfonic or theophylline acetic acid addition. salts, as well as the 8-halotheophyllines, for example 8-bromo-theophylline. In embodiments, inorganic acid addition salts, including but not limited to, hydrochloric, hydrobromic, hydroiodic, sulfuric, sulfamic, phosphoric or nitric acid addition salts may be used.

In embodiments, ethyl-cyclopent-3-ene-carboxylate (10), (3R,4S)-ethyl-3-((tert-butoxycarbonyl)amino)-4-(hydroxy) cyclopentane carboxylate (11), (3R)-ethyl-3-((tert-butoxycarbonyl)amino)-4-oxo-cyclopentane carboxylate (12); ethyl (9S)-9-(tert-butoxycarbonylamino)-1,4-dioxa-7-spiro[4.4]nonanecarboxylate (13), ethyl (S)-9-(tert-butoxycarbonylamino)-1,4-dioxa-7-spiro[4.4]nonene-7-carboxylate (14), or ethyl (S)-3-((tert-butoxycarbonyl)amino)-4-(difluoromethylene)cyclopent-1-ene-1-carboxylate (15) may be provided as an acid addition salt, a zwitter ion hydrate, zwitter ion anhydrate, hydrochloride or hydrobromide salt, or in the form of the zwitter ion monohydrate. Acid addition salts, include but are not limited to, maleic, fumaric, benzoic, ascorbic, succinic, oxalic, bis-methylenesalicylic, methanesulfonic, ethane-disulfonic, acetic, propionic, tartaric, salicylic, citric, gluconic, lactic, malic, mandelic, cinnamic, citraconic, aspartic, stearic, palmitic, itaconic, glycolic, pantothenic, p-amino-benzoic, glutamic, benzene sulfonic or theophylline acetic acid addition salts, as well as the 8-halotheophyllines, for example 8-bromo-theophylline. In embodiments, inorganic acid addition salts, including but not limited to, hydrochloric, hydrobromic, hydroiodic, sulfuric, sulfamic, phosphoric or nitric acid addition salts may be used.

In embodiments, pharmaceutical compositions include various dosage forms including conventional formulations and modified release formulations. Such pharmaceutical compositions may be adapted for any suitable route of administration, e.g., oral, rectal, nasal, ophthalmic, pulmonary, vaginal, sublingual, transdermal, intravenous, intraarterial, intramuscular, intraperitoneal and subcutaneous routes. Suitable dosage forms include tablets, capsules, oral liquids, ophthalmic drops, ophthalmic ointments, ophthalmic gels, powders, aerosols, transdermal modalities such as topical liquids, patches, creams and ointments, parenteral formulations and suppositories.

In embodiments, as mentioned previously, pharmaceutical compositions herein may be provided with conventional release or modified release profiles. Pharmaceutical compositions may be prepared using a pharmaceutically acceptable "carrier" composed of materials that are considered safe and effective. The "carrier" includes all components present in the pharmaceutical formulation other than the active ingredient or ingredients. The term "carrier" includes, but is not limited to, diluents, binders, lubricants, disintegrants, fillers, and coating compositions. Those with skill in the art are familiar with such pharmaceutical carriers and methods of compounding pharmaceutical compositions using such carriers.

In embodiments, pharmaceutical compositions herein are modified release dosage forms which provide modified release profiles. Modified release profiles may exhibit immediate release, delayed release, or extended release profiles. Conventional (or unmodified) release oral dosage forms such as tablets, capsules, suppositories, syrups, solutions and suspensions typically release medications into the mouth, stomach or intestines as the tablet, capsule shell or suppository dissolves, or, in the case of syrups, solutions and suspensions, when they are swallowed. The pattern of drug release from modified release (MR) dosage forms is deliberately changed from that of a conventional dosage form to achieve a desired therapeutic objective and/or better patient compliance. Types of MR drug products include orally disintegrating dosage forms (ODDFs) which provide immediate release, extended release dosage forms, delayed release dosage forms (e.g., enteric coated), and pulsatile release dosage forms.

An ODDF is a solid dosage form containing a medicinal substance or active ingredient which disintegrates rapidly, usually within a matter of seconds when placed upon the tongue. The disintegration time for ODDFs generally range from one or two seconds to about a minute. ODDFs are designed to disintegrate or dissolve rapidly on contact with saliva. This mode of administration can be beneficial to people who may have problems swallowing tablets whether it be from physical infirmity or psychiatric in nature. Some subjects with an eye disorder may exhibit such behavior. ODDF's can provide rapid delivery of medication to the blood stream through mucosa resulting in a rapid onset of action. Examples of ODDFs include orally disintegrating tablets, capsules and rapidly dissolving films and wafers.

Extended release dosage forms (ERDFs) have extended release profiles and are those that allow a reduction in dosing frequency as compared to that presented by a conventional dosage form, e.g., a solution or unmodified release dosage form. ERDFs provide a sustained duration of action of a drug. Suitable formulations which provide extended release profiles are well-known in the art. For example, coated slow release beads or granules ("beads" and "granules" are used interchangeably herein) in which any of the compounds described herein are applied to beads, e.g., confectioners nonpareil beads, and then coated with conventional release retarding materials such as waxes, enteric coatings and the like. In embodiments, beads can be formed in which any of the compounds described herein are mixed with a material to provide a mass from which the compound leaches out. In embodiments, the beads may be engineered to provide different rates of release by varying characteristics of the coating or mass, e.g., thickness, porosity, using different materials, etc. Beads having different rates of release may be combined into a single dosage form to provide variable or continuous release. The beads can be contained in capsules or compressed into tablets.

In embodiments, modified dosage forms herein incorporate delayed release dosage forms having delayed release profiles. Delayed release dosage forms can include delayed release tablets or delayed release capsules. A delayed release tablet is a solid dosage form which releases a compound (or compounds) described herein are at a time other than promptly after administration. A delayed release capsule is a solid dosage form in which the drug is enclosed within either a hard or soft soluble container made from a suitable form of gelatin, and which releases a drug (or drugs) at a time other than promptly after administration. For example, enteric-coated tablets, capsules, particles and beads are well-known examples of delayed release dosage forms. Enteric coated tablets, capsules and particles and beads pass through the stomach and release the drug in the intestine. In embodiments, a delayed release tablet is a solid dosage form containing a conglomerate of medicinal particles that releases a drug (or drugs) at a time other than promptly after administration. In embodiments, the conglomerate of medicinal particles are covered with a coating which delays release of the drug. In embodiments, a delayed release capsule is a solid dosage form containing a conglomerate of medicinal particles that releases a drug (or drugs) at a time other than promptly after administration. In embodiments, the conglomerate of medicinal particles are covered with a coating which delays release of the drug.

Delayed release dosage forms are known to those skilled in the art. For example, coated delayed release beads or granules in which any of the compounds described herein are applied to beads, e.g., confectioners nonpareil beads, and then coated with conventional release delaying materials such as waxes, enteric coatings and the like. In embodiments, beads can be formed in which any of the compounds described herein are mixed with a material to provide a mass from which the drug leaches out. In embodiments, the beads may be engineered to provide different rates of release by varying characteristics of the coating or mass, e.g., thickness, porosity, using different materials, etc. In embodiments, enteric coated granules of any of the compounds described herein can be contained in an enterically coated capsule or tablet which releases the granules in the small intestine. In embodiments, the granules have a coating which remains intact until the coated granules reach at least the ileum and thereafter provide a delayed release of the drug in the colon. Suitable enteric coating materials are well known in the art, e.g., Eudragit® coatings such methacrylic acid and methyl methacrylate polymers and others. The granules can be contained in capsules or compressed into tablets.

In embodiments, any of the compounds described herein are incorporated into porous inert carriers that provide delayed release profiles. In embodiments, the porous inert carriers incorporate channels or passages from which the drug diffuses into surrounding fluids. In embodiments, any of the compounds described herein are incorporated into an ion-exchange resin to provide a delayed release profile. Delayed action may result from a predetermined rate of release of the drug from the resin when the drug-resin complex contacts gastrointestinal fluids and the ionic constituents dissolved therein. In embodiments, membranes are utilized to control rate of release from drug containing reservoirs. In embodiments, liquid preparations may also be utilized to provide a delayed release profile. For example, a liquid preparation consisting of solid particles dispersed throughout a liquid phase in which the particles are not soluble. The suspension is formulated to allow at least a reduction in dosing frequency as compared to that drug presented as a conventional dosage form (e.g., as a solution or a prompt drug-releasing, conventional solid dosage form). For example, a suspension of ion-exchange resin constituents or microbeads.

In embodiments, pharmaceutical compositions described herein are suitable for ophthalmic or parenteral administration, including, e.g., intramuscular (i.m.), intravenous (i.v.), subcutaneous (s.c.), intraperitoneal (i.p.), or intrathecal (i.t.). Parenteral or ophthalmic compositions must be sterile for administration by injection, infusion, instillation or implantation into the body and may be packaged in either single-dose or multi-dose containers. In embodiments, liquid pharmaceutical compositions for ophthalmic or parenteral administration to a subject include an active substance, e.g., any of the compounds described herein are in any of the respective amounts described above. In embodiments, the pharmaceutical compositions for ophthalmic or parenteral administration are formulated as a total volume of about, e.g., 1 ml, 2 ml, 3 ml, 4 ml, 5 ml, 7.5 ml, 10 ml, 20 ml, 25 ml, 50 ml, 100 ml, 200 ml, 250 ml, or 500 ml. In embodiments, the compositions are contained in a bag, a glass vial, a plastic vial, or a bottle.

In embodiments, pharmaceutical compositions for ophthalmic or parenteral administration include respective amounts described above for any of the compounds described herein. In embodiments, pharmaceutical compositions for ophthalmic or parenteral administration include about 0.0001 mg to about 500 mg of any of the compounds described herein. In embodiments, pharmaceutical compositions for ophthalmic or parenteral administration to a subject may include any of the compounds described herein, at a respective concentration of about 0.005 mg/ml to about 500 mg/ml. In embodiments, the pharmaceutical composition for ophthalmic or parenteral administration includes any of the compounds described herein at a respective concentration of, e.g., about 0.05 mg/ml to about 50 mg/ml, about 0.1 mg/ml to about 50 mg/ml, about 0.1 mg/ml to about 10 mg/ml, about 0.05 mg/ml to about 25 mg/ml, about 0.05 mg/ml to about 10 mg/ml, about 0.05 mg/ml to about 5 mg/ml, or about 0.05 mg/ml to about 1 mg/ml. In embodiments, the pharmaceutical composition for ophthalmic or parenteral administration includes any of the compounds described herein at a respective concentration of, e.g., about 0.05 mg/ml to about 15 mg/ml, about 0.5 mg/ml to about 10 mg/ml, about 0.25 mg/ml to about 5 mg/ml, about 0.5 mg/ml to about 7 mg/ml, about 1 mg/ml to about 10 mg/ml, about 5 mg/ml to about 10 mg/ml, or about 5 mg/ml to about 15 mg/ml.

In embodiments, a pharmaceutical composition for ophthalmic or parenteral administration is provided wherein the pharmaceutical composition is stable for at least six months. In embodiments, the pharmaceutical compositions for ophthalmic or parenteral administration exhibit no more than about 5% decrease in active substance, e.g., (S)-3-amino-4-(difluoromethylenyl)cyclopent-1-ene-1-carboxylic acid, or a pharmaceutically acceptable salt of thereof, e.g., 3 months or 6 months. In embodiments, the amount of ((S)-3-amino-4-(difluoromethylenyl)cyclopent-1-ene-1-carboxylic acid, or a pharmaceutically acceptable salt thereof, degrades at no more than about, e.g., 2.5%, 1%, 0.5% or 0.1%. In embodiments, the degradation is less than about, e.g., 5%, 2.5%, 1%, 0.5%, 0.25%, 0.1%, for at least six months.

In embodiments, pharmaceutical compositions for ophthalmic or parenteral administration are provided wherein the pharmaceutical composition remains soluble. In embodiments, pharmaceutical compositions for ophthalmic or parenteral administration are provided that are stable, soluble, local site compatible and/or ready-to-use. In embodiments, the pharmaceutical compositions herein are ready-to-use for direct administration to a subject in need thereof.

The pharmaceutical compositions for ophthalmic or parenteral administration provided herein may include one or more excipients, e.g., solvents, solubility enhancers, suspending agents, buffering agents, isotonicity agents, stabilizers or antimicrobial preservatives. When used, the excipients of the ophthalmic or parenteral compositions will not adversely affect the stability, bioavailability, safety, and/or efficacy of any of the compounds described herein used in the composition. Thus, ophthalmic or parenteral compositions are provided wherein there is no incompatibility between any of the components of the dosage form.

In embodiments, ophthalmic or parenteral compositions including any of the compounds described herein include a stabilizing amount of at least one excipient. For example, excipients may be selected from the group consisting of buffering agents, solubilizing agents, tonicity agents, antioxidants, chelating agents, antimicrobial agents, and preservatives. One skilled in the art will appreciate that an excipient may have more than one function and be classified in one or more defined group.

In embodiments, ophthalmic or parenteral compositions any of the compounds described herein and an excipient wherein the excipient is present at a weight percent (w/v) of less than about, e.g., 10%, 5%, 2.5%, 1%, or 0.5%. In embodiments, the excipient is present at a weight percent between about, e.g., 1.0% to 10%, 10% to 25%, 15% to 35%, 0.5% to 5%, 0.001% to 1%, 0.01% to 1%, 0.1% to 1%, or 0.5% to 1%. In embodiments, the excipient is present at a weight percent between about, e.g., 0.001% to 1%, 0.01% to 1%, 1.0% to 5%, 10% to 15%, or 1% to 15%.

In embodiments, ophthalmic or parenteral compositions of any of the compounds described herein are provided, wherein the pH of the composition is between about 4.0 to about 8.0. In embodiments, the pH of the compositions is between, e.g., about 5.0 to about 8.0, about 6.0 to about 8.0, about 6.5 to about 8.0. In embodiments, the pH of the compositions is between, e.g., about 6.5 to about 7.5, about 7.0 to about 7.8, about 7.2 to about 7.8, or about 7.3 to about 7.6. In embodiments, the pH of the aqueous solution is, e.g., about 6.8, about 7.0, about 7.2, about 7.4, about 7.6, about 7.7, about 7.8, about 8.0, about 8.2, about 8.4, or about 8.6.

In embodiments, pharmaceutical compositions including (S)-3-amino-4-(difluoromethylenyl)cyclopent-1-ene-1-carboxylic acid, or a pharmaceutically acceptable salt thereof, provide an in vivo plasma profile having a $C_{max}$ of (S)-3-amino-4-(difluoromethylenyl)cyclopent-1-ene-1-carboxylic acid less than about, e.g., 2000 ng/ml, 1000 ng/ml, 850 ng/ml, 800 ng/ml, 750 ng/ml, 700 ng/ml, 650 ng/ml, 600 ng/ml, 550 ng/ml, 450 ng/ml, 400 ng/ml 350 ng/ml, or 300 ng/ml. In embodiments, the pharmaceutical composition provides an in vivo plasma profile having a $C_{max}$ less than about, e.g., 250 ng/ml, 200 ng/ml 150 ng/ml, or 100 ng/ml.

In embodiments, provided herein are pharmaceutical compositions containing (S)-3-amino-4-(difluoromethylenyl)cyclopent-1-ene-1-carboxylic acid, or a pharmaceutically acceptable salt thereof and one or more of any of the compounds described herein, wherein the composition provides a consistent in vivo plasma profile of (S)-3-amino-4-(difluoromethylenyl)cyclopent-1-ene-1-carboxylic acid having a $AUC_{0-\infty}$ of less than about 900 ng·hr/ml.

In embodiments, the $T_{max}$ of pharmaceutical compositions containing (S)-3-amino-4-(difluoromethylenyl)cyclopent-1-ene-1-carboxylic acid, or a pharmaceutically acceptable salt thereof and one or more of any of the compounds described herein is less than 3 hours. In embodiments, the $T_{max}$ of the pharmaceutical composition is less than 2.5 hours. In embodiments, the $T_{max}$ of the pharmaceutical composition is less than 2 hours. In embodiments, the $T_{max}$ of the pharmaceutical composition is less than 1.5 hours. In embodiments, the $T_{max}$ of the pharmaceutical composition is less than 1 hour. In embodiments, the $T_{max}$ of the pharmaceutical composition is less than 0.5 hour. In embodiments, the $T_{max}$ of the pharmaceutical composition is less than 0.25 hour.

In embodiments, pharmaceutical compositions containing (S)-3-amino-4-(difluoromethylenyl)cyclopent-1-ene-1-carboxylic acid, or a pharmaceutically acceptable salt thereof and one or more of any of the compounds described herein provide a dissolution of at least about 80% within the first 20 minutes of administration to a subject in need thereof. In embodiments, pharmaceutical compositions containing (S)-3-amino-4-(difluoromethylenyl)cyclopent-1-ene-1-carboxylic acid, or a pharmaceutically acceptable salt thereof and one or more of any of the compounds described herein provide a dissolution of at least about, e.g., 85%, 90% or 95% within the first 20 minutes of administration to a subject in need thereof. In embodiments, pharmaceutical compositions containing (S)-3-amino-4-(difluoromethylenyl)cyclopent-1-ene-1-carboxylic acid, or a pharmaceutically acceptable salt thereof and one or more of any of the compounds described herein provide a dissolution of at least 80% within the first 10 minutes of administration to a subject in need thereof.

It should be understood that respective amounts of (S)-3-amino-4-(difluoromethylenyl)cyclopent-1-ene-1-carboxylic acid, or a pharmaceutically acceptable salt thereof and one or more of any of the compounds described herein are applicable to all the dosage forms described herein including conventional dosage forms, modified dosage forms, as well as the ophthalmic and parenteral formulations described herein. Those skilled in the art will determine appropriate amounts depending on criteria such as dosage form, route of administration, subject tolerance, efficacy, therapeutic goal and therapeutic benefit, among other pharmaceutically acceptable criteria.

Unless defined otherwise, all technical and scientific terms used herein have the same meanings as commonly understood by one of skill in the art to which the disclosure herein belongs.

The term "about" or "approximately" as used herein means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, up to 10%, up to 5%, and/or up to 1% of a given value. Alternatively, particularly with respect to biological systems or processes, the term can mean within an order of magnitude, preferably within 5-fold, and more preferably within 2-fold, of a value.

"PK" refers to the pharmacokinetic profile. $C_{max}$ is defined as the highest plasma drug concentration estimated during an experiment (ng/ml). $T_{max}$ is defined as the time when $C_{max}$ is estimated (min). $AUC_{0-\infty}$ is the total area under the plasma drug concentration-time curve, from drug administration until the drug is eliminated (ng·hr/ml). The area under the curve is governed by clearance. Clearance is defined as the volume of blood or plasma that is totally cleared of its content of drug per unit time (ml/min).

"Pharmaceutically acceptable" refers to molecular entities and compositions that are "generally regarded as safe"— e.g., that are physiologically tolerable and do not typically produce an allergic or similar untoward reaction, such as gastric upset and the like, when administered to a human. In embodiments, this term refers to molecular entities and compositions approved by a regulatory agency of the federal or a state government, as the GRAS list under section 204(s) and 409 of the Federal Food, Drug and Cosmetic Act, that is subject to premarket review and approval by the FDA or similar lists, the U.S. Pharmacopeia or another generally recognized pharmacopeia for use in animals, and more particularly in humans.

"Effective amount" or "therapeutically effective amount" means a dosage sufficient to alleviate one or more symptoms of a disorder, disease, or condition being treated.

"Co-administered with", "co-therapy", "in combination with", "a combination of", "combined with" or "administered along with" may be used interchangeably and mean that two or more agents are administered in the course of therapy. The agents may be administered together at the same time or separately in spaced apart intervals. The agents may be administered in a single dosage form or in separate dosage forms.

"Patient in need thereof" includes individuals that have been diagnosed with a disease, condition or disorder for which treatment with (S)-3-amino-4-(difluoromethylenyl) cyclopent-1-ene-1-carboxylic acid, or a pharmaceutically acceptable salt thereof is indicated. "Patient" and "subject" are used interchangeably herein.

EXAMPLES

The Examples provided herein are included solely for augmenting the disclosure herein and should not be considered to be limiting in any respect.

Methods In General (1R,4S)-2-Azabicyclo[2.2.1]hept-5-en-3-one (2) was purchased from Acella Chembio, San Diego, CA 92121. 2-((difluoromethyl)sulfinyl)pyridine (20) was either purchased from Enamine Chemicals, Monmouth Jct., NJ 08852, or synthesized from diethyl bromodifluoromethylphosphonate and 2-mercaptopyridine. See, Zhou, Q.; Ruffoni, A.; Gianatassio, R.; Fujiwara, Y.; Sella, E.; Shabat, D.; Baran, P. S. Angew. Chem. Int. Ed. 2013, 52, 3949-3952. All other reagents were purchased from Sigma-Aldrich or Acros Organics and used without further purification. Anhydrous solvents (THF, $CH_2Cl_2$, DMF) were purified before use by passing through a column composed of activated alumina and a supported copper redox catalyst. Yields refer to chromatographically and spectroscopically ($^1$H-NMR) homogeneous material. Analytical thin-layer chromatography (TLC) was performed using Merck Silica Gel 60 Å F-254 precoated plates (0.25 mm thickness), and components were visualized by ultraviolet light (254 nm) and/or ceric ammonium molybdate stain. Flash column chromatography was performed on a Teledyne Combiflash Rf Plus automated flash purification system with various Teledyne cartridges (4-80 g, 40-63 μm, 60 Å). Purifications were performed with hexanes and ethyl acetate unless otherwise noted. $^1$H and $^{13}$C NMR spectra were recorded on a Bruker Avance-III NMR spectrometer at 500 MHz and 126 MHz, respectively, in $CDCl_3$ or $D_2O$. Chemical shifts were reported in ppm, multiplicities are indicated by s=singlet, d=doublet, t=triplet, q=quartet, sep=septet, dd=doublet of doublet, dt=doublet of triplet, m=multiplet, br=broad resonance. Coupling constants were reported in Hz. High resolution mass spectral data were obtained on an Agilent 6210 LC-TOF spectrometer in the positive ion mode using electrospray ionization with an Agilent G1312 Å HPLC pump and an Agilent G1367B autoinjector at the Integrated Molecular Structure Education and Research Center (IMSERC), Northwestern University. Analytical HPLC was performed by using a reserved-phase Agilent Infinity 1260 HPLC with a Phenomenex Kintex C-18 column (50×2.1 mm, 2.6 μm), detecting with UV absorbance at 254 nm.

Example 1

Manufacture of (1R,4S)-2-(4-Methoxybenzyl)-2-azabicyclo[2.2.1]hept-5-en-3-one (3)

4-Methoxybenzyl alcohol (35.80 mL, 0.29 mol, 1.5 equiv) was added dropwise to concentrated HCl (300 mL) and stirred for 1 h. Water was added, and the liquid was extracted (2×100 mL) with diethyl ether. The diethyl ether was dried over $Na_2SO_4$ and concentrated to a volume of about 50 mL. To a 2 L flask, equipped with an addition funnel, was added (1R,4S)-2-azabicyclo[2.2.1]hept-5-en-3-one (21.00 g, 0.19 mol), DMF (600 mL), and THF (600 mL), and the flask was cooled to 0° C. NaH (8.45 g, 0.21 mol, 1.1 equiv, 60% dispersion in mineral oil) was added portionwise. The flask was placed under N2 and stirred for 30 min. The Et2O/PMBCl solution was transferred to the addition funnel and was added dropwise at 0° C. The reaction was stirred for 6 h at room temperature. Upon completion, THF was removed in vacuo, and diethyl ether and water were added. Any solids were filtered, and the layers were separated. The aqueous layer was extracted (3×100 mL) with diethyl ether, and the organic layers were combined and washed with brine (2×200 mL). After drying over Na2SO4 and concentration, a yellow oil was obtained. The crude oil was purified by flash chromatography to yield 32.2 g (0.14 mol, 73% yield) of protected (1R,4S)-2-azabicyclo[2.2.1]hept-5-en-3-one (3). Spectra matched those in the literature. See, Qiu, J.; Silverman, R. B. *J. Med. Chem.* 2000, 43, 706-720.

Example 2

Manufacture of (1R,4R,6S,7R)-7-Bromo-2-(4-methoxybenzyl)-3-oxo-2-azabicyclo[2.2.1]heptan-6-yl acetate (4)

To a solution of (1R,4S)-2-(4-Methoxybenzyl)-2-azabicyclo[2.2.1]hept-5-en-3-one (3), (10.00 g, 43.62 mmol) in AcOH (110.0 mL) was added 1,3-dibromo-5,5-dimethylhydantoin (7.48 g, 26.17 mmol, 0.6 equiv). The reaction was stirred for 6 h, and upon completion, water was added. The aqueous layer was extracted with diethyl ether (3×200 mL), and the organic layers were combined, washed with 1 M NaOH, dried over $Na_2SO_4$, and concentrated. Purification by flash chromatography yielded (1R,4R,6S,7R)-7-bromo-2-(4-methoxybenzyl)-3-oxo-2-azabicyclo[2.2.1]heptan-6-yl acetate (4) (14.40 g, 39.25 mmol, 90% yield) as a thick oil. Spectra matched those in the literature. See, Qiu, J.; Silverman, R. B. *J. Med. Chem.* 2000, 43, 706-720.

Example 3

Manufacture of (1R,4R,7R)-7-Bromo-2-(4-methoxybenzyl)-2-azabicyclo[2.2.1]heptane-3,6-dione (5)

Method A (1R,4R,6S,7R)-7-Bromo-2-(4-methoxybenzyl)-3-oxo-2-azabicyclo[2.2.1]heptan-6-yl acetate (4) (12.8 g, 34.7 mmol) was dissolved in MeOH (270 mL) and $K_2CO_3$ (14.40 g, 104.28 mmol, 3.0 equiv) was added. The reaction was stirred for 1 h, filtered, and then concentrated. Ethyl acetate and water were added, and the layers were separated. The organic layer was dried over $Na_2SO_4$ and concentrated to yield an off-white colored solid, which was used directly in the next step.

This compound was placed in a 500 mL flask and purged with argon. Dichloromethane (170 mL) was added followed by 4 Å molecular sieves (10 g). TPAP (122.2 mg, 0.35 mmol. 0.01 equiv) and NMO (8.14 g, 69.52 mmol, 2.0 equiv) were then added, and the reaction mixture was stirred overnight. The reaction mixture was then filtered and concentrated to a volume of 20 mL and loaded directly onto a flash chromatography column. The resulting yellowish solid can be recrystallized from hexanes/ethyl acetate to obtain a white powder (5.96 g, 18.38 mmol, 52% yield). Spectra matched those in the literature. See, Qiu, J.; Silverman, R. B. *J. Med. Chem.* 2000, 43, 706-720.

Method B (1R,4R,6S,7R)-7-Bromo-2-(4-methoxybenzyl)-3-oxo-2-azabicyclo[2.2.1]heptan-6-yl acetate (4) (25.5 g, 69.2 mmol) was dissolved in MeOH (300 mL) and $K_2CO_3$ (30 g, 0.23 mol, 3 equiv) was added. The reaction was stirred for 1 h, filtered, and then concentrated. Ethyl acetate and water were added, and the layers were separated. The organic layer was dried over $Na_2SO_4$ and concentrated to yield an off-white colored solid, which was used directly in the next step. A three-neck flask was equipped with a vent line to a bubble, dropping funnel with nitrogen inlet, and septum. Dichloromethane (160 mL) was added, and the flask was purged with nitrogen. Oxalyl chloride (8.40 mL, 98.0 mmol, 1.4 equiv) was added, and the reaction was cooled to −78° C.

DMSO (11.60 mL, 0.16 mol, 2.3 equiv) was added to the addition funnel and then added dropwise slowly at a rate to control the vigorous gas evolution. After addition, the reaction was stirred at −78° C. for 10 min. The deacylated material was dissolved in dichloromethane (160 mL) and added slowly to the reaction via addition funnel. The reaction was stirred for 10 min at −78° C. Triethylamine (68.3 mL, 0.49 mol, 7 equiv) was then added dropwise via addition funnel. Upon completion, the reaction was stirred at −78° C. for 10 min, warmed to room temp, and quenched with 1 M HCl. After separation, the organic layer was dried over $Na_2SO_4$ and concentrated in a fume hood. Purification via flash chromatography yielded (1R,4R,7R)-7-Bromo-2-(4-methoxybenzyl)-2-azabicyclo[2.2.1]heptane-3,6-dione (5) as a beige solid (13.5 g, 41.7 mmol, 60% yield).

Example 4

Manufacture of (1R,4R,7R)-7-Bromo-6-(difluoromethylene)-2-(4-methoxybenzyl)-2-azabicyclo[2.2.1]heptan-3-one (6)

Figure 2:
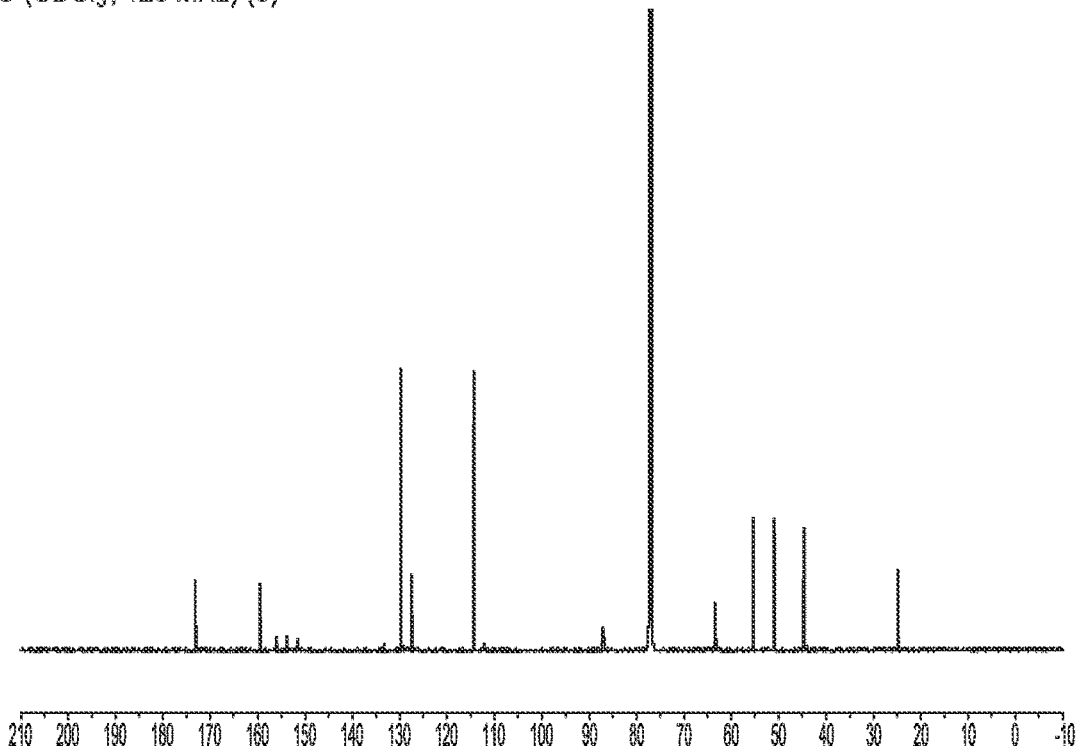
FIG. 2 is a $^{13}$C NMR spectrum (CDCl$_3$; 126 MHz) of (1R,4R,7R)-7-bromo-6-(difluoromethylene)-2-(4-methoxybenzyl)-2-azabicyclo[2.2.1]heptan-3-one (6).
Figure 3:
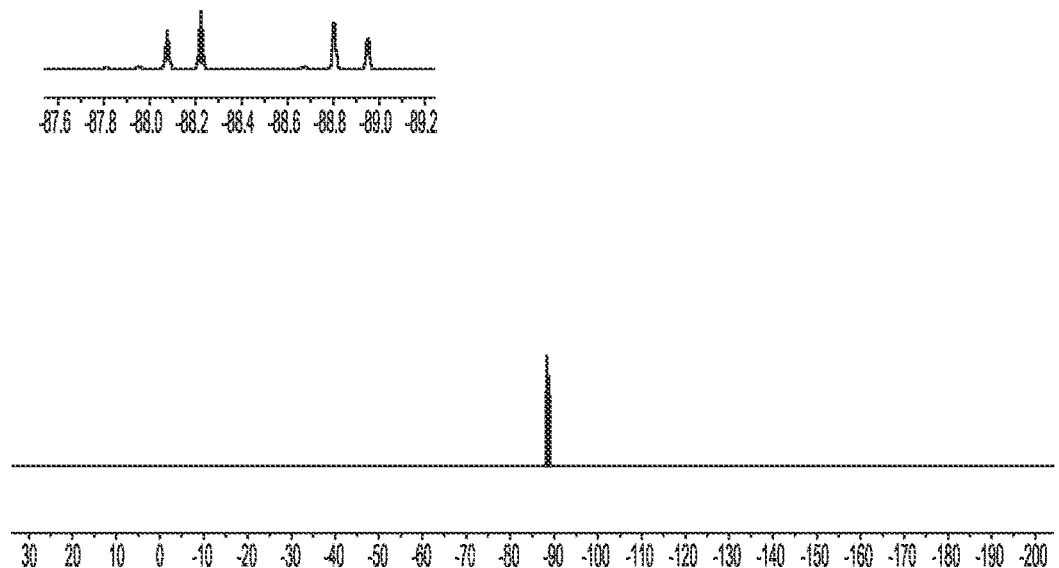
FIG. 3 is a 127.5 MHz $^{19}$F NMR spectrum (CDCl$_3$) of (1R,4R,7R)-7-bromo-6-(difluoromethylene)-2-(4-methoxybenzyl)-2-azabicyclo[2.2.1]heptan-3-one (6).

(1R,4R,7R)-7-Bromo-2-(4-methoxybenzyl)-2-azabicyclo[2.2.1]heptane-3,6-dione (5) (1.00 g, 3.09 mmol) and 2-((difluoromethyl)sulfinyl)pyridine (20), 715.10 mg, 3.70 mmol, 1.2 equiv) were added to a round bottom flask and purged with argon. DMF (15 mL) was added, and the reaction was cooled to between −55 and −65° C. KO$^t$Bu (623.0 mg, 5.55 mmol, 1.8 equiv, 0.5 M in DMF) was added via syringe pump over 1 h. The temperature was maintained between −55 and −65° C. After addition was complete, the reaction was further stirred for 30 min at −60° C. Saturated $NH_4Cl$ (5.00 mL) was added, and the reaction was stirred for 5 min at −60° C. before 6 M HCl (5.00 mL) was added. After 5 min of stirring at −60° C., the reaction mixture was warmed to room temperature and then to 65° C. for 1 h. After being cooled, the reaction was diluted with brine, extracted with ethyl acetate (2×20 mL), and washed with brine (10 mL). Drying over $Na_2SO_4$ and concentration yielded a yellow oil, which was purified via flash chromatography to yield a white solid (620.0 mg, 1.73 mmol, 58% yield). $[\alpha]_D^{23°\ C.}$=−46.6 4 (c 0.80, $CHCl_3$); m.p. 85-87° C.; $^1H$ NMR (500 MHz, $CDCl_3$) δ 7.14 (d, J=8.4 Hz, 1H), 6.86 (d, J=8.5 Hz, 1H), 4.60 (d, J=14.6 Hz, 1H), 4.19 (s, OH), 4.14 (s, OH), 3.90 (d, J=14.7 Hz, 1H), 3.79 (s, 1H), 3.00 (s, OH), 2.83 (dq, J=14.6, 3.0 Hz, 1H), 2.27 (d, J=15.2 Hz, 1H). See, FIG. 1. $^{13}C$ NMR (126 MHz, CDCl3) δ 173.0, 159.5, 153.9 (dd, J=287.5, 283.8 Hz), 129.7, 127.5, 114.3, 87.1 (dd, J=24.9, 23.5 Hz), 63.4, 63.3, 55.3, 50.8 (d, J=17.1 Hz), 44.6, 24.8. See, FIG. 2. $^{19}F$ NMR (376 MHz, $CDCl_3$) δ−88.15 (dp, J=55.1, 2.7 Hz), −88.88 (dq, J=54.8, 2.8 Hz). See, FIG. 3. IR (film, $cm^{-1}$) 3013, 1785, 1683, 1551; HMRS (ESI$^+$) calc'd for $C_{15}H_{14}BrF_2NO_2$+Na$^+$: 380.0074; found 380.0075.

Example 5

Manufacture of (1R,4R,7R)-7-Bromo-6-(difluoromethylene)-2-azabicyclo[2.2.1]heptan-3-one (7)

(1R,4R,7R)-7-Bromo-6-(difluoromethylene)-2-(4-methoxybenzyl)-2-azabicyclo[2.2.1]heptan-3-one (6) (140 mg, 0.39 mmol) was added to MeCN (2.0 mL) and cooled to 0° C. Ceric ammonium nitrate (643.5 mg, 1.17 mmol, 3 equiv) in $H_2O$ (0.75 mL) was added dropwise. The reaction was allowed to warm to room temperature and stirred for 1 h.

Figure 4:
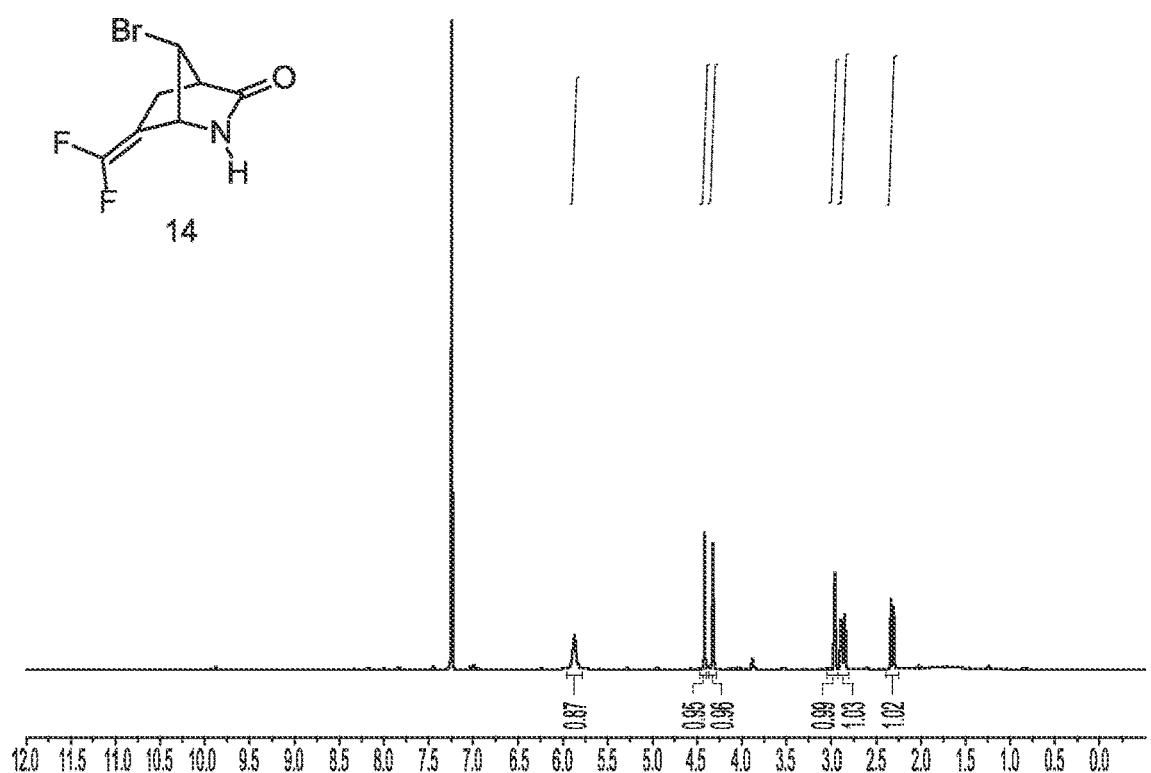
FIG. 4 is a 500 MHz $^1$H NMR spectrum (CDCl$_3$) of (1R,4R,7R)-7-Bromo-6-(difluoromethylene)-2-azabicyclo[2.2.1]heptan-3-one (7).
Figure 5:
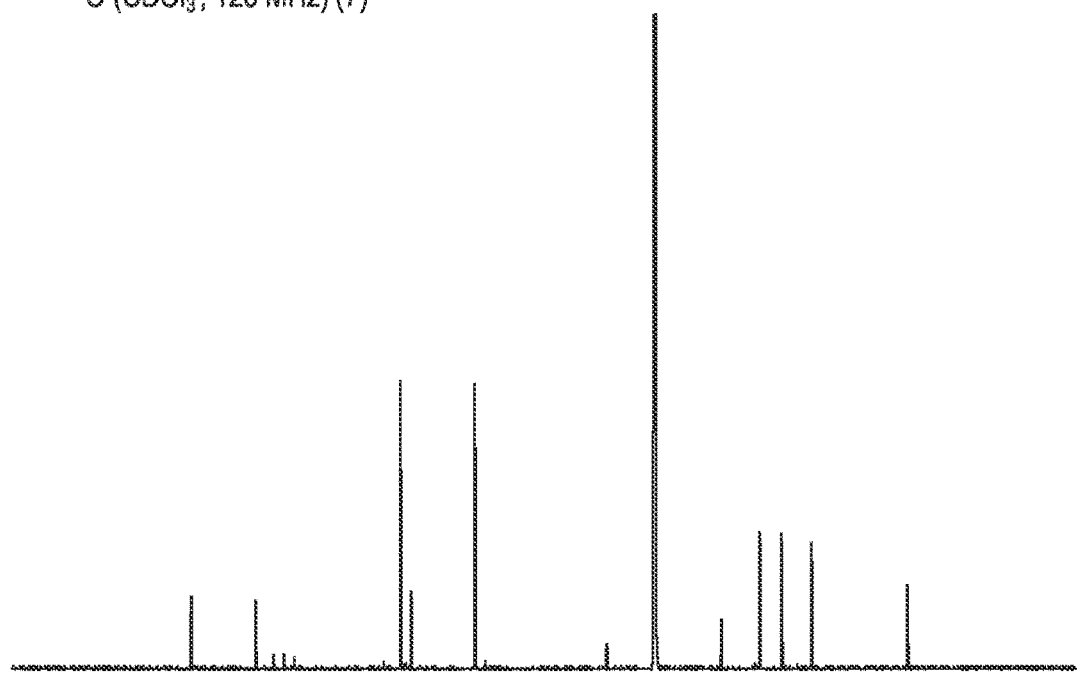
FIG. 5 is a $^{13}$C NMR spectrum (CDCl$_3$; 126 MHz) of (1R,4R,7R)-7-Bromo-6-(difluoromethylene)-2-azabicyclo[2.2.1]heptan-3-one (7).
Figure 6:
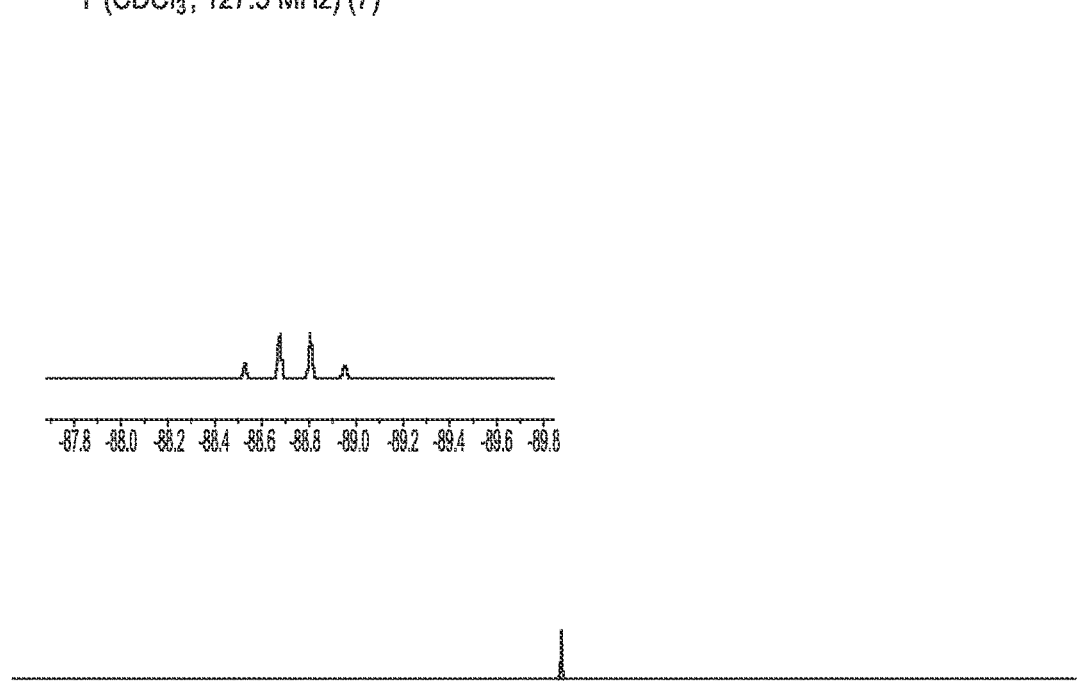
FIG. 6 is a 127.5 MHz $^{19}$F NMR spectrum of (1R,4R,7R)-7-Bromo-6-(difluoromethylene)-2-azabicyclo[2.2.1]heptan-3-one (7) (CDCl$_3$).

After completion, water was added, and the solution was extracted with ethyl acetate (2×15 mL). The organic layers were dried over Na2SO4 and concentrated under reduced pressure. Flash chromatography yielded (1R,4R,7R)-7-bromo-6-(difluoromethylene)-2-azabicyclo[2.2.1]heptan-3-one (7) as a white solid (75 mg, 0.315 mmol, 80% yield). $[\alpha]_D^{23°\,C.}$=+38.5 (c 0.90, CHCl3); m.p. 139-141° C.; $^1$H NMR (500 MHz, CDCl$_3$) δ 5.87 (s, 1H), 4.41 (s, 1H), 4.32 (s, 1H), 2.96 (s, 1H), 2.87 (dq, J=15.4, 3.4 Hz, 1H), 2.32 (d, J=0.15.2 Hz, 1H). See, FIG. 4. $^{13}$C NMR (126 MHz, CDCl$_3$) δ 174.9, 153.5 (t, J=287.5 Hz), 88.7 (t, J=24.1 Hz), 60.6, 51.5, 50.3, 24.3. See, FIG. 5. $^{19}$F NMR (376 MHz, CDCl$_3$) δ−88.60 (dq, J=55.1, 2.8 Hz), −88.88 (dp, J=54.6, 2.5 Hz). See, FIG. 6. IR (film, cm$^{-1}$) 3249. 1788, 1678, 1397; HMRS (ESI$^+$) calc'd for C$_7$H$_6$BrF$_2$NO+H$^+$: 237.9679; found 237.9678.

Example 6

Manufacture of (1R,4R,7R)-7-Bromo-6-(difluoromethylene)-2-(tert-butoxycarbonyl)-2-azabicyclo [2.2.1]heptan-3-one (8) and Methyl (S)-3-((tert-butoxycarbonyl)amino)-4-(difluoromethylene) cyclopent-1-ene-1-carboxylate (9)

Figure 7:
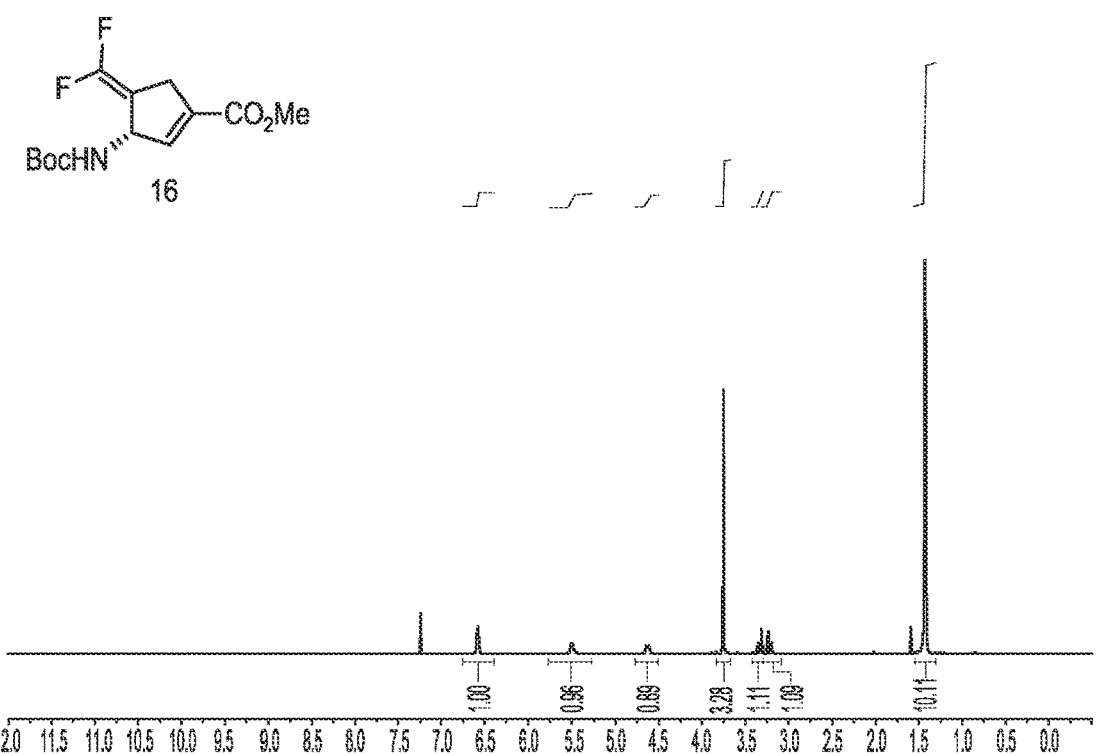
FIG. 7 is a 500 MHz $^1$H NMR spectrum (CDCl$_3$) of methyl (S)-3-((tert-butoxycarbonyl)amino)-4-(difluoromethylene)cyclopent-1-ene-1-carboxylate (9).
Figure 8:
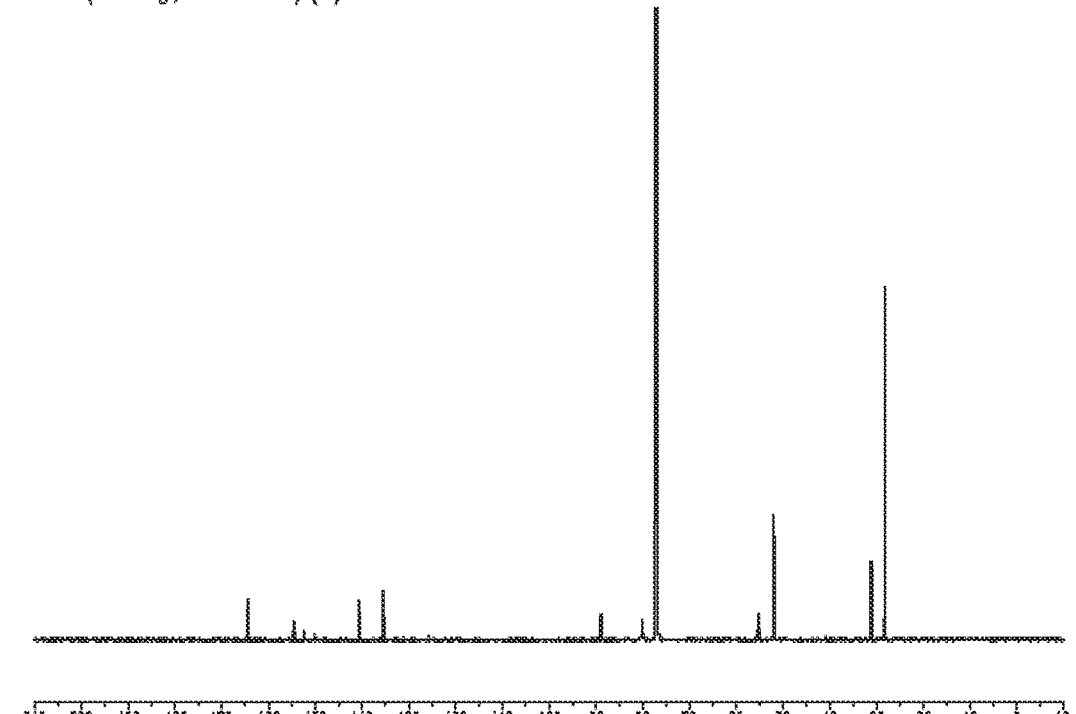
FIG. 8 is a $^{13}$C NMR spectrum (CDCl$_3$; 126 MHz) of methyl (S)-3-((tert-butoxycarbonyl)amino)-4-(difluoromethylene)cyclopent-1-ene-1-carboxylate (9).
Figure 9:
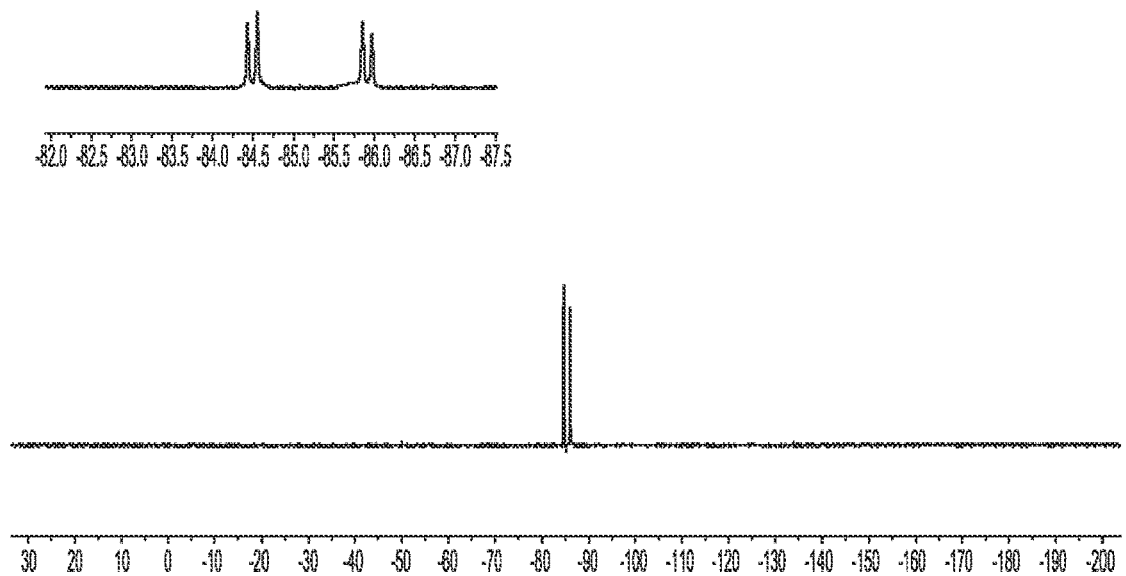
FIG. 9 is a 127.5 MHz $^{19}$F NMR spectrum of methyl (S)-3-((tert-butoxycarbonyl)amino)-4-(difluoromethylene)cyclopent-1-ene-1-carboxylate (9).

(1R,4R,7R)-7-Bromo-6-(difluoromethylene)-2-azabicyclo[2.2.1]heptan-3-one (7) (890.0 mg, 3.74 mmol) was added to dichloromethane (18.0 mL) followed by the sequential addition of Boc$_2$O (978.8 mg, 4.49 mmol, 1.2 equiv), DMAP (45.7 mg, 0.37 mmol, 0.1 equiv), and Et$_3$N (0.78 mL, 5.61 mmol, 1.5 equiv). The reaction was stirred for 1 h and then was washed with 1 M HCl (10 mL), dried over Na$_2$SO$_4$, and concentrated. The resulting oil containing (1R,4R,7R)-7-Bromo-6-(difluoromethylene)-2-(tert-butoxycarbonyl)-2-azabicyclo[2.2.1]heptan-3-one (8) was dissolved in methanol (18.0 mL), then K$_2$CO$_3$ (1.55 g, 11.21 mmol, 3.0 equiv) was added, and the reaction was stirred for 6 h. After completion, as indicated by LC/MS (methanolysis of the lactam occurs in the first 10 min), the reaction was diluted with brine and extracted with ethyl acetate (3×200 mL). Upon drying over Na$_2$SO$_4$, concentrating, and purification by flash chromatography, methyl (S)-3-((tert-butoxycarbonyl)amino)-4-(difluoromethylene)cyclopent-1-ene-1-carboxylate (9) was obtained as a white solid (570 mg, 1.97 mmol, 52% yield). $[\alpha]_D^{23°\,C.}$=+104.8 (c 0.50, CHCl$_3$); m.p. 95-97° C.; 1H NMR (500 MHz, CDCl$_3$) δ 6.58 (s, 1H), 5.50 (d, J=9.1 Hz, 1H), 4.63 (d, J=8.7 Hz, 1H), 3.75 (s, 3H), 3.33 (d, J=20.4 Hz, 1H), 3.21 (dd, J=20.3, 2.7 Hz, 1H), 1.45 (s, 9H). See, FIG. 7. $^{13}$C NMR (126 MHz, CDCl$_3$) δ 164.3, 154.7, 154.6, 152.4 (t, J=288.5 Hz), 150.1, 140.6, 135.5, 88.9 (dd, J=21.8, 20.2 Hz), 80.1, 55.3, 51.9, 31.1, 28.3. See, FIG. 8. $^{19}$F NMR (376 MHz, CDCl$_3$) δ−84.49 (d, J=43.6 Hz), −85.91 (d, J=43.4 Hz). See, FIG. 9. IR (film, cm$^{-1}$) 3347, 2987, 1773, 1681; HMRS (ESI$^+$) calc'd for C$_{13}$H$_{17}$F$_2$NO4+Na$^+$: 312.1023; found 312.1018.

Example 7

Manufacture of (S)-3-Amino-4-(difluoromethylene) cyclopent-1-ene-1-carboxylic acid hydrochloride (1)

Figure 10:
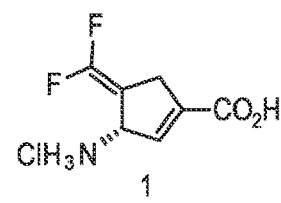
FIG. 10 is a 500 MHz $^1$H NMR spectrum (CDCl$_3$) (S)-3-amino-4-(difluoromethylenyl)cyclopent-1-ene-1-carboxylic acid (1).
Figure 11:
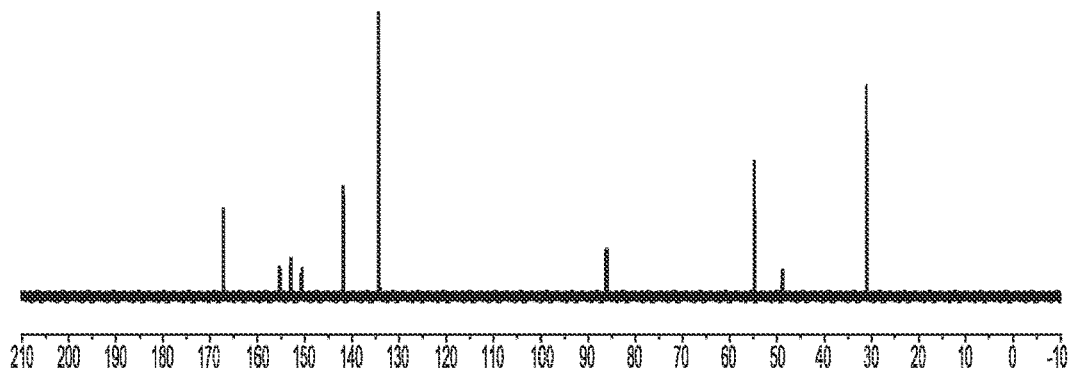
FIG. 11 is a $^{13}$C NMR spectrum (CDCl$_3$; 126 MHz) of (S)-3-amino-4-(difluoromethylenyl)cyclopent-1-ene-1-carboxylic acid (1).
Figure 12:
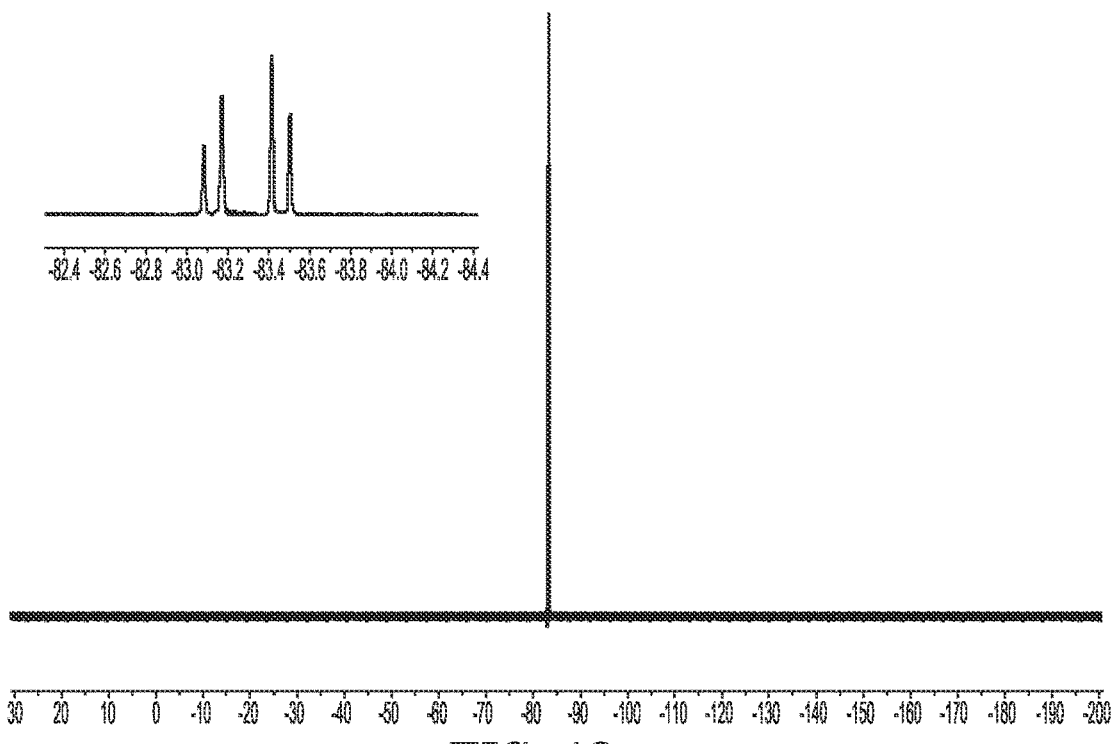
FIG. 12 is a 127.5 MHz $^{19}$F NMR spectrum of (S)-3-amino-4-(difluoromethylenyl)cyclopent-1-ene-1-carboxylic acid (1).

Methyl (S)-3-((tert-butoxycarbonyl)amino)-4-(difluoromethylene)cyclopent-1-ene-1-carboxylate (9) (570.0 mg, 1.97 mmol) was dissolved in dioxane (1.00 mL), and 6 M HCl (9 mL) was added. After heating at 80° C. for 2 h, the reaction was concentrated to yield (S)-3-Amino-4-(difluoromethylene)cyclopent-1-ene-1-carboxylic acid hydrochloride (1) as a light brown powder (403.0 mg, 1.90 mmol, 97% yield). Crystallization from ethanol/diethyl ether increased purity to >99%. $[\alpha]_D^{23°\,C.}$=+67.2 (c 0.90, H$_2$O); m.p. 207° C. (decomp.); $^1$H NMR (500 MHz, D$_2$0) 6 6.59 (s, 1H), 4.70 (s, 13H), 3.39 (d, J=20.5 Hz, 1H), 3.33 (d, J=20.8 Hz, 1H). See, FIG. 10. $^3$C NMR (126 MHz, D$_2$0) 6 167.2, 153.0 (dd, J=290.1, 288.4 Hz), 141.8, 134.3, 86.1 (dd, J=26.6, 21.2 Hz), 54.8 (d, J=5.7 Hz), 31.1. See, FIG. 11. $^{19}$F NMR (470 MHz, D$_2$0) 6-83.1 (dq, J=40.8, 2.8 Hz), −83.5 (dq, J=40.4, 2.1 Hz). See, FIG. 12. IR (film, cm$^{-1}$) 3348, 3075, 2981, 2883, 2829, 2600, 2434, 1771, 1686; HMRS (ESI-) calc'd for C$_7$H$_7$F$_2$NO$_2$—H: 174.0372; found 174.0369.

It should be understood that the examples and embodiments provided herein are exemplary examples and embodiments. Those skilled in the art will envision various modifications of the examples and embodiments that are consistent with the scope of the disclosure herein. Such modifications are intended to be encompassed by the claims.

What is claimed is:

1. A pharmaceutical composition comprising (S)-3-amino-4-(difluoromethylenyl)cyclopent-1-ene-1-carboxylic acid (1), or a pharmaceutically acceptable salt thereof, and one or more of the following compounds: (1R,4S)-2-azabicyclo[2.2.1]hept-5-en-3-one (2), (1R,4S)-2-(4-methoxybenzyl)-2-azabicyclo[2.2.1]hept-5-en-3-one (3), (1R,4R,6S, 7R)-7-bromo-2-(4-methoxybenzyl)-3-oxo-2-azabicyclo [2.2.1]heptan-6-yl acetate (4), (1R,4R,6S,7R)-7-bromo-6-hydroxy-2-(4-methoxybenzyl)-2-azabicyclo[2.2.1]heptan-3-one (25), (1R,4R,7R)-7-bromo-2-(4-methoxybenzyl)-2-azabicyclo[2.2.1]heptane-3,6-dione (5), (1R,4R,7R)-7-bromo-6-(difluoromethylene)-2-(4-methoxybenzyl)-2-azabicyclo[2.2.1]heptan-3-one (6), (1R,4R,7R)-7-bromo-6-(difluoromethylene)-2-azabicyclo[2.2.1]heptan-3-one (7), (1R,4R,7R)-7-bromo-6-(difluoromethylene)-2-(tert-butoxycarbonyl)-2-azabicyclo[2.2.1]heptan-3-one (8), methyl (S)-3-((tert-butoxycarbonyl)amino)-4-(difluoromethylene)cyclopent-1-ene-1-carboxylate (9), ethyl (S)-3-((tert-butoxycarbonyl)amino)-4-(difluoromethylene)cyclopent-1-ene-1-carboxylate (15), and (S)-3-((tert-butoxycarbonyl)amino)-4-(difluoromethylene)cyclopent-1-ene-1-carboxylic acid (19), or a pharmaceutically acceptable salt of any of the preceding compounds.

2. The pharmaceutical composition of claim 1 comprising (S)-3-amino-4-(difluoromethylenyl)cyclopent-1-ene-1-carboxylic acid (1), or a pharmaceutically acceptable B salt thereof, and from 0.0001 to 1 mg of (1R,4S)-2-azabicyclo [2.2.1]hept-5-en-3-one (2), or a pharmaceutically acceptable salt thereof.

3. The pharmaceutical composition of claim 1 comprising (S)-3-amino-4-(difluoromethylenyl)cyclopent-1-ene-1-carboxylic acid (1), or a pharmaceutically acceptable salt thereof, and from 0.0001 to 1 mg of (1R,4S)-2-(4-methoxybenzyl)-2-azabicyclo[2.2.1]hept-5-en-3-one (3), or a pharmaceutically acceptable salt thereof.

4. The pharmaceutical composition of claim 1 comprising (S)-3-amino-4-(difluoromethylenyl)cyclopent-1-ene-1-carboxylic acid (1), or a pharmaceutically acceptable B salt thereof, and from 0.0001 to 1 mg of (1R,4R,6S,7R)-7-bromo-2-(4-methoxybenzyl)-3-oxo-2-azabicyclo[2.2.1]heptan-6-yl acetate (4), or a pharmaceutically acceptable salt thereof.

5. The pharmaceutical composition of claim 1 comprising (S)-3-amino-4-(difluoromethylenyl)cyclopent-1-ene-1-carboxylic acid (1), or a pharmaceutically acceptable B salt thereof, and from 0.0001 to 1 mg of (1R,4R,7R)-7-bromo-6-hydroxy-2-(4-methoxybenzyl)-2-azabicyclo[2.2.1]heptan-3-one (25), or a pharmaceutically acceptable salt thereof.

6. The pharmaceutical composition of claim 1 comprising (S)-3-amino-4-(difluoromethylenyl)cyclopent-1-ene-1-carboxylic acid (1), or a pharmaceutically acceptable B salt thereof, and from 0.0001 to 1 mg of (1R,4R,7R)-7-bromo-2-(4-methoxybenzyl)-2-azabicyclo[2.2.1]heptane-3,6-dione (5), or a pharmaceutically acceptable salt thereof.

7. The pharmaceutical composition of claim 1 comprising (S)-3-amino-4-(difluoromethylenyl)cyclopent-1-ene-1-carboxylic acid (1), or a pharmaceutically acceptable B salt thereof, and from 0.0001 to 1 mg of (1R,4R,7R)-7-bromo-6-(difluoromethylene)-2-(4-methoxybenzyl)-2-azabicyclo[2.2.1]heptan-3-one (6), or a pharmaceutically acceptable salt thereof.

8. The pharmaceutical composition of claim 1 comprising (S)-3-amino-4-(difluoromethylenyl)cyclopent-1-ene-1-carboxylic acid (1), or a pharmaceutically acceptable salt thereof, and from 0.0001 to 1 mg of (1R,4R,7R)-7-bromo-6-(difluoromethylene)-2-azabicyclo[2.2.1]heptan-3-one (7), or a pharmaceutically acceptable salt thereof.

9. The pharmaceutical composition of claim 1 comprising (S)-3-amino-4-(difluoromethylenyl)cyclopent-1-ene-1-carboxylic acid (1), or a pharmaceutically acceptable salt thereof, and from 0.0001 to 1 mg of (1R,4R,7R)-7-bromo-6-(difluoromethylene)-2-(tert-butoxycarbonyl)-2-azabicyclo[2.2.1]heptan-3-one (8), or a pharmaceutically acceptable salt thereof.

10. The pharmaceutical composition of claim 1 comprising (S)-3-amino-4-(difluoromethylenyl)cyclopent-1-ene-1-carboxylic acid (1), or a pharmaceutically acceptable salt thereof, and from 0.0001 to 1 mg methyl of (S)-3-((tert-butoxycarbonyl)amino)-4-(difluoromethylene)cyclopent-1-ene-1-carboxylate (9), or a pharmaceutically acceptable salt thereof.

11. The pharmaceutical composition of claim 1 comprising (S)-3-amino-4-(difluoromethylenyl)cyclopent-1-ene-1-carboxylic acid (1), or a pharmaceutically acceptable B salt thereof, and from 0.0001 to 1 mg of ethyl (S)-3-((tert-butoxycarbonyl)amino)-4-(difluoromethylene)cyclopent-1-ene-1-carboxylate (15), or a pharmaceutically acceptable salt thereof.

12. The pharmaceutical composition of claim 1 comprising (S)-3-amino-4-(difluoromethylenyl)cyclopent-1-ene-1-carboxylic acid (1), or a pharmaceutically acceptable salt thereof, and from 0.0001 to 1 mg of (S)-3-((tert-butoxycarbonyl)amino)-4-(difluoromethylene )cyclopent-1-ene-1-carboxylic acid (19), or a pharmaceutically acceptable salt thereof.

* * * * *